(12) United States Patent
Dieck et al.

(10) Patent No.: US 12,377,107 B2
(45) Date of Patent: Aug. 5, 2025

(54) NT5C2 INHIBITORS FOR THE TREATMENT OF CHEMOTHERAPY-RESISTANT ACUTE LYMPHOBLASTIC LEUKEMIA

(71) Applicant: THE TRUSTEES OF COLUMBIA UNIVERSITY IN THE CITY OF NEW YORK, New York, NY (US)

(72) Inventors: Chelsea Dieck, New York, NY (US); Adolfo Ferrando, New York, NY (US); Arie Zask, New York, NY (US); Brent Stockwell, New York, NY (US)

(*) Notice: Subject to any disclaimer, the term of this patent is extended or adjusted under 35 U.S.C. 154(b) by 825 days.

(21) Appl. No.: 17/644,187

(22) Filed: Dec. 14, 2021

(65) Prior Publication Data
US 2022/0105105 A1 Apr. 7, 2022

Related U.S. Application Data

(63) Continuation of application No. PCT/US2020/037741, filed on Jun. 15, 2020.

(60) Provisional application No. 62/861,867, filed on Jun. 14, 2019.

(51) Int. Cl.
| | |
|---|---|
| A61K 31/5415 | (2006.01) |
| A61K 31/381 | (2006.01) |
| A61K 31/4025 | (2006.01) |
| A61K 31/4184 | (2006.01) |
| A61K 31/428 | (2006.01) |
| A61K 31/4704 | (2006.01) |
| A61K 45/06 | (2006.01) |
| C07D 217/26 | (2006.01) |
| C07D 333/66 | (2006.01) |
| C07D 401/06 | (2006.01) |
| C07D 401/14 | (2006.01) |
| C07D 409/12 | (2006.01) |
| C07D 417/12 | (2006.01) |
| C07D 471/04 | (2006.01) |
| C07D 495/04 | (2006.01) |

(52) U.S. Cl.
CPC ........ *A61K 31/5415* (2013.01); *A61K 31/381* (2013.01); *A61K 31/4025* (2013.01); *A61K 31/4184* (2013.01); *A61K 31/428* (2013.01); *A61K 31/4704* (2013.01); *A61K 45/06* (2013.01); *C07D 217/26* (2013.01); *C07D 333/66* (2013.01); *C07D 401/06* (2013.01); *C07D 401/14* (2013.01); *C07D 409/12* (2013.01); *C07D 417/12* (2013.01); *C07D 471/04* (2013.01); *C07D 495/04* (2013.01)

(58) Field of Classification Search
CPC .............. A61K 31/5415; A61K 31/381; A61K 31/4025; A61K 31/4184; A61K 31/428; A61K 31/4704; A61K 45/06; C07D 217/26; C07D 333/66; C07D 401/06; C07D 409/12; C07D 417/12; C07D 471/04; C07D 496/04
See application file for complete search history.

(56) References Cited

U.S. PATENT DOCUMENTS

| 2016/0272632 A1* | 9/2016 | Childers | ............. C07D 471/04 |
| 2016/0272643 A1* | 9/2016 | Chaloin | .................. A61P 35/02 |

FOREIGN PATENT DOCUMENTS

| WO | 2016/081947 A2 | 5/2016 |
| WO | 2018/067834 A1 | 4/2018 |
| WO | 2018/183928 A1 | 10/2018 |

OTHER PUBLICATIONS

Reglero et al, Pharmacological Inhibition of NT5C2 reverses genetic and non-genetic drivers of 6-MP resistance in acute lymphoblastic leukemia, Cancer Discov. Nov. 2, 2022; 12(11):2646-2665 (Year: 2022).*
Reglero et al, Pharmacological Inhibition of NT5C2 reverses genetic and non-genetic drivers of 6-MP resistance in acute lymphoblastic leukemia, Cancer Discov. Nov. 2, 2022; 12(11): Supplemental Data (Year: 2022).*
Database Registry, "1-[(1,2-dihydro-1-oxo-4-isoquinolinyl)carbonyl]-4-phenyl-4-Piperidinecarbonitrile", XP093102802, retrieved from Database accession No. 1609884-19-6, Jun. 6, 2014, 1 page.
Database Registry, "4-[[4-(2-pyrrolidinyl)-1-piperidinyl]carbonyl]-1(2H)-Isoquinolinone", XP093102798, retrieved from Database accession No. 2248949-01-9, Nov. 18, 2018, 1 page.

(Continued)

*Primary Examiner* — Noble E Jarrell
*Assistant Examiner* — Phillip Matthew Rzeczycki
(74) *Attorney, Agent, or Firm* — Wolter Van Dyke Davis, PLLC; Eugene J. Molinelli; Timothy H. Van Dyke

(57) ABSTRACT

Various embodiments relate to compounds, having structures according to Structure A or Structure B, as specified herein. The compounds according to various embodiments may inhibit NT5C2 nucleotidase. The compounds according to various embodiments may synergistically decrease cell viability of NT5C2 R367Q mutant lymphoblasts when used in combination with 6-mercaptopurine (6-MP) to treat a cancer. The cancer may be, but is not limited to, acute lymphoblastic leukemia. Various embodiments relate to a compositions that may include one or more compounds according to any embodiment described herein or a pharmaceutically acceptable salt or derivative thereof and a pharmaceutically acceptable carrier. Various embodiments relate to methods of treating cancer. The method may comprise administering a therapeutically effective amount of one or more compounds according to any embodiment described herein or a pharmaceutically acceptable salt or derivative thereof.

17 Claims, 28 Drawing Sheets

(56) References Cited

OTHER PUBLICATIONS

Database Registry, "N-[3-(aminocarbonyl)-4,5,6,7-tetrahydrobenzo[b]thien-2-yl]-1H-Benzimidazole-6-carboxaminde", XP093102822, retrieved from Database accession No. 941185-83-7, Jul. 4, 2007, 1 page.
European Search Report and Search Opinion received for EP Application No. 20823573.9, mailed on Dec. 1, 2023, 7 pages.
International Preliminary Report on Patentability received for PCT Patent Application No. PCT/US2020/037741, mailed on Dec. 23, 2021, 7 pages.
International Search Report and Written Opinion received for PCT Patent Application No. PCT/US2020/037741, mailed on Sep. 9, 2020, 8 pages.
Pubchem, Substance Record for SID 334036251, Available Date: Apr. 25, 2017 [retrieved on Aug. 26, 2020). Retrieved from the Internet: <URL: https://pubchem.ncbi.nlm.nih.gov/substance/334036251>.
Pubchem, Substance Record for SID 383046115, Available Date: Apr. 26, 2019 (retrieved on Aug. 10, 11, 26, 2020). Retrieved from the Internet: <URL: https://pubchem.ncbi.nlm.nih.gov/substance/383046115>.

\* cited by examiner

NT5C2 INHIBITORS FOR THE TREATMENT OF CHEMOTHERAPY-RESISTANT ACUTE LYMPHOBLASTIC LEUKEMIA

CROSS-REFERENCE TO RELATED APPLICATION

This application is a continuation of PCT Appln. No. PCT/US20/37741 filed Jun. 15, 2020 which claims the benefit of U.S. Provisional Patent Application No. 62/861,867, filed Jun. 14, 2019, titled NT5C2 INHIBITORS FOR THE TREATMENT OF CHEMOTHERAPY-RESISTANT ACUTE LYMPHOBLASTIC LEUKEMIA (ALL), which is incorporated by reference herein in its entirety.

STATEMENT REGARDING FEDERALLY SPONSORED RESEARCH OR DEVELOPMENT

This invention was made with government support under CA216981 awarded by the National Institutes of Health. The government has certain rights in the invention.

BACKGROUND

T-cell acute lymphoblastic leukemia (T-ALL) is an aggressive, hematologic malignancy accounting for 20% of adult and 10-15% of childhood acute lymphoblastic leukemia (ALL) cases. Relapsed T-ALL has a high rate of secondary chemotherapy resistance. Gain of function mutations in the cytosolic nucleotidase 2 gene (NT5C2) are detected in 45% of early relapse T-ALL cases and in 20% of T-ALL relapses overall. Therefore, NT5C2 inhibitors can potentially treat T-ALL and relapsed T-ALL by enhancing the efficacy of existing chemotherapy treatments.

The discussion of shortcomings and needs existing in the field prior to the present invention is in no way an admission that such shortcomings and needs were recognized by those skilled in the art prior to the present disclosure.

BRIEF SUMMARY

Various embodiments relate to a compound, having the structure:

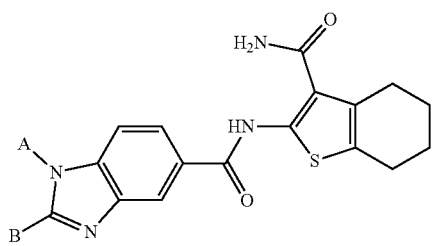

Structure A

According to various embodiments A and B may be any suitable substituent. For example, according to various embodiments, A may be selected from hydrogen and methyl and B may be selected from hydrogen and methyl.

Various embodiments relate to a compound, having the structure:

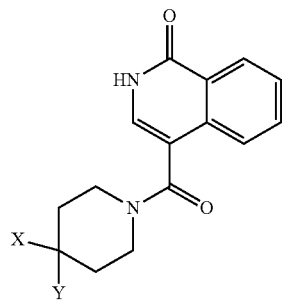

Structure B

According to various embodiments X and Y may be any suitable substituent. For example, according to various embodiments, X may be selected from hydrogen and

and Y may be selected from the group consisting of

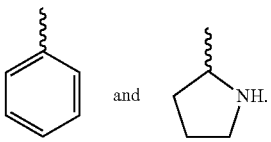

The compound according to various embodiments may inhibit NT5C2 nucleotidase. The compounds according to various embodiments may synergistically decrease cell viability of NT5C2 R367Q mutant lymphoblasts when used in combination with 6-mercaptopurine (6-MP) to treat a cancer. The cancer may be, but is not limited to, acute lymphoblastic leukemia.

Various embodiments relate to a composition comprising a compound according to any embodiment described herein or a pharmaceutically acceptable salt or derivative thereof and a pharmaceutically acceptable carrier.

Various embodiments relate to methods of treating cancer. The method may comprise administering a therapeutically effective amount of a compound according to any embodiment described herein or a pharmaceutically acceptable salt or derivative thereof. The compound may be administered by any suitable technique. The cancer may be, but is not limited to, acute lymphoblastic leukemia.

These and other features, aspects, and advantages of various embodiments will become better understood with reference to the following description, figures, and claims.

BRIEF DESCRIPTION OF THE FIGURES

Many aspects of this disclosure can be better understood with reference to the following figures.

FIG. 34A is an example according to various embodiments, illustrating inhibitory activity of HTP_2 against recombinant NT5C2 R367Q protein in malachite green assays.

FIG. 34B is an example according to various embodiments, illustrating surface plasmon resonance analysis (Biacore) of HTP_2 interaction with recombinant NT5C2 protein.

FIG. 34C is an example according to various embodiments, illustrating 6-MP responses in isogenic mouse T-ALL lymphoblasts with a wild type Nt5c2 (NT5C2+/co-R367Q) or a mutant Nt5c2 genotype (Nt5c2+/R367Q) measured as cell viability in presence of increasing concentrations of the HTP_2 NT5C2 inhibitor.

FIG. 34D is an example according to various embodiments, illustrating quantification of cell viability in isogenic mouse T-ALL lymphoblasts with a wild type Nt5c2 (NT5C2+/co-R367Q) or a mutant Nt5c2 genotype (Nt5c2+/R367Q) measured as cell viability in presence of 6-MP and increasing concentrations of the HTP_2 NT5C2 inhibitor.

FIG. 34E is an example according to various embodiments, illustrating response to 6-MP measured as cell viability in human T-ALL cells (CUTLL1) expressing wild type NT5C2 in basal conditions and in presence of the HTP_2 NT5C2 inhibitor.

FIG. 34F is an example according to various embodiments, illustrating response to 6-MP measured as cell viability in human T-ALL cells (CUTLL1) expressing mutant NT5C2 R367Q in basal conditions and in presence of the HTP_2 NT5C2 inhibitor.

FIG. 34G is an example according to various embodiments, illustrating response to 6-MP measured as cell viability in human T-ALL cells (CUTLL1) expressing mutant NT5C2 R238W in basal conditions and in presence of the HTP_2 NT5C2 inhibitor.

FIG. 34H is an example according to various embodiments, illustrating response to 6-MP measured as cell viability in human T-ALL cells (CUTLL1) expressing mutant NT5C2 L375F in basal conditions and in presence of the HTP_2 NT5C2 inhibitor.

FIG. 34I is an example according to various embodiments, illustrating response to 6-MP measured as cell viability in human T-ALL cells (JURKAT) infected with an empty vector control in basal conditions and in presence of the HTP_2 NT5C2 inhibitor.

FIG. 34J is an example according to various embodiments, illustrating response to 6-MP measured as cell viability in human T-ALL cells (JURKAT) infected with an vector expressing wild type NT5C2 in basal conditions and in presence of the HTP_2 NT5C2 inhibitor.

FIG. 34K is an example according to various embodiments, illustrating response to 6-MP measured as cell viability in human T-ALL cells (JURKAT) infected with an vector expressing mutant NT5C2 R367Q in basal conditions and in presence of the HTP_2 NT5C2 inhibitor.

FIG. 35A is an example according to various embodiments, illustrating inhibitory activity of HTP_47 against recombinant NT5C2 R367Q protein in malachite green assays.

FIG. 35I is an example according to various embodiments, illustrating response to 6-MP measured as cell viability in human T-ALL cells (JURKAT) infected with a vector expressing wild type NT5C2 in basal conditions and in presence of the HTP_47 NT5C2 inhibitor.

FIG. 35P is an example according to various embodiments, illustrating response to 6-MP measured as cell viability in human T-ALL cells (JURKAT) infected with a vector expressing mutant NT5C2 R367Q in basal conditions and in presence of the HTP_47 NT5C2 inhibitor.

FIG. 38A is an example according to various embodiments, illustrating inhibitory activity of compound 83424890 presented in Formula 34 against recombinant NT5C2 R367Q protein in malachite green assays.

FIG. 38P is an example according to various embodiments, illustrating response to 6-MP measured as cell viability in human T-ALL cells (JURKAT) infected with a vector expressing mutant NT5C2 R367Q in basal conditions and in presence of the NT5C2 inhibitor compound 83424890 presented in Formula 34.

Figure 1:
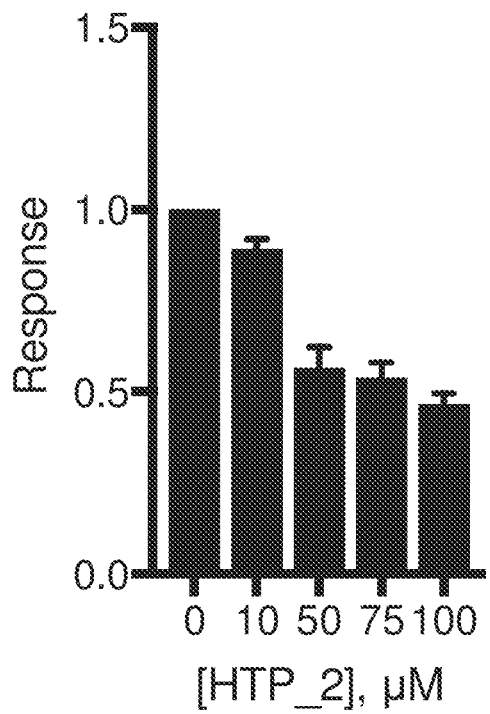
FIG. 1 is an example according to various embodiments, illustrating the NT5C2 inhibition response for varying amounts (μM) of a compound according to Formula 1 (HTP_2).

It should be understood that the various embodiments are not limited to the examples illustrated in the figures.

DETAILED DESCRIPTION

Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, the term "standard temperature and pressure" generally refers to 25° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent" or "mole percent" generally refers to the percentage that the moles of a particular component are of the total moles that are in a mixture. The sum of the mole fractions for each component in a solution is equal to 1.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, an "adjunct cancer therapeutic agent" pertains to an agent, other than the novel NT5C2 inhibitors described herein, that possesses selectively cytotoxic or cytostatic effects to cancer cells over normal cells. In a specific example, the adjunct cancer therapeutic agent is purine analog such as but not limited to cladribine, tioguanine, clofarabine, mercaptopurine (e.g. 6-MP), fludarabine, and nelarabine. Adjunct cancer therapeutic agents may be co-administered with an enumerated NT5C2 inhibitor.

The terms "administering" or "administer" or "administration" as used herein with respect to an agent means providing the agent to a subject using any of the various methods or delivery systems for administering agents or pharmaceutical compositions known to those skilled in the art. Modes of administering include, but are not limited to oral administration, parenteral administration such as intravenous, subcutaneous, intramuscular or intraperitoneal injections, rectal administration by way of suppositories, transdermal administration, intraocular administration or administration by any route or method that delivers a therapeutically effective amount of the drug or composition to the cells or tissue to which it is targeted. Alternatively, routine experimentation will determine other acceptable routes of administration.

The term "chemotherapy-resistant acute lymphoblastic leukemia" refers to acute lymphoblastic leukemia (ALL) in which cancer cells are resistant to thio-purine (e.g. 6-mercaptopurine) chemotherapy. Alternatively, or additionally, "Chemotherapy-resistant acute lymphoblastic leukemia" includes ALL in which cancer cells harbor one or more mutations of NT5C2 that disrupt intramolecular switch off mechanisms responsible for returning the enzyme to its resting inactive state after activation and lock the NT5C2 protein in an active state similar to that induced by allosteric activators.

The term "enumerated compound(s)" as used herein encompass(es), for example, any NT5C2 inhibitor compound disclosed herein including any pharmaceutically acceptable salt or solvate thereof. Specific examples of compounds of the invention include those according to any chemical structure presented herein and any subgenera and/or species, or a pharmaceutically acceptable salt or solvate thereof. Enumerated compound includes the disclosed structure or a stereoisomer thereof.

The terms "heterocyclyl", "heterocycle", "heterocyclic", and the like refer to substituted or unsubstituted non-aromatic ring structures, preferably 3- to 8-membered rings, whose ring structures include at least one heteroatom, preferably one to four heteroatoms, more preferably one or two heteroatoms. The terms "heterocyclyl," "heterocyclic," and the like also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "solvate" as used herein means a compound formed by solvation (the combination of solvent molecules with molecules or ions of the solute), or an aggregate that consists of a solute ion or molecule, i.e., enumerated compound, with one or more solvent molecules. When water is the solvent, the corresponding solvate is a "hydrate." Examples of hydrate include, but are not limited to, hemihydrate, monohydrate, dihydrate, trihydrate, hexahydrate, etc. It should be understood by one of ordinary skill in the art that the present compound and/or the pharmaceutically acceptable salt of the present compound may also exist in a solvate form. The solvate is typically formed via hydration which is either part of the preparation of the present compound or through natural absorption of moisture by the anhydrous compound of the present invention.

The term "synergistically" or "synergistic effect" is intended to have its ordinary meaning to one of skill in the art. A synergistic effect produced by a combination of compounds can include an effect which is observed to be greater than the effect produced by each compound individually. For example, in the case of NT5C2 inhibitors that synergistically decrease cell viability of cancer cells when used in combination with 6-mercaptopurine (6-MP) to treat a cancer, the NT5C2 inhibitor and 6-MP have a mutual enhancing of the effect of each individual compound by the combination of compounds that produces more than additive effect. In certain instances, two or more compounds having a synergistic effect allows for lower doses of the individual compounds when co-administered to produce the same or greater therapeutic effect or outcome compared to higher doses of the compound administered singly. The term "co-administer" or other grammatical forms thereof, as used herein refers to the administration of an active agent before, concurrently, or after the administration of another active agent such that the biological effects of either agents overlap.

The terms "subject," "individual," "host," and "patient," are used interchangeably herein to refer to an animal being treated with one or more enumerated compounds as taught herein, including, but not limited to, simians, humans, avians, felines, canines, equines, rodents, bovines, porcines, ovines, caprines, mammalian farm animals, mammalian sport animals, and mammalian pets. A suitable subject for the invention can be any animal, preferably a human, that is suspected of having, has been diagnosed as having, or is at risk of developing a disease that can be ameliorated, treated or prevented by administration of one or more enumerated compounds.

The term "substituted" refers to moieties having substituents replacing a hydrogen on one or more carbons of the backbone. It will be understood that "substitution" or "substituted with" includes the implicit proviso that such substitution is in accordance with the permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

As used herein, the term "substituent," may include, but is not limited to, H, cyano, oxo, nitro, acyl, acylamino, halogen, hydroxy, amino acid, amine, amide, carbamate, ester, ether, carboxylic acid, thio, thioalkyl, thioester, thioether, C1-8 alkyl, C1-8alkoxy, C1-8alkenyl, C1-8aralkyl, 3- to 8-membered carbocyclic, 3- to 8-membered heterocyclic, 3- to 8-membered aryl, or 3- to 8-membered heteroaryl, sulfate, sulfonamide, sulfoxide, sulfonate, sulfone, alkylsulfonyl, or arylsulfonyl.

The term "treating" or "treatment of" as used herein refers to providing any type of medical management to a subject. Treating includes, but is not limited to, administering a composition comprising one or more active agents to a subject using any known method for purposes such as curing, reversing, alleviating, reducing the severity of, inhibiting the progression of, or reducing the likelihood of a disease, disorder, or condition or one or more symptoms or manifestations of a disease, disorder or condition.

A "therapeutically effective amount" refers to an amount which, when administered in a proper dosing regimen, is sufficient to reduce or ameliorate the severity, duration, or progression of the disorder being treated (e.g., cancer), prevent the advancement of the disorder being treated (e.g., cancer), cause the regression of the disorder being treated (e.g., cancer), or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

Unless specifically stated as "unsubstituted," references to chemical moieties herein are understood to include substituted variants. For example, reference to an "aryl" group or moiety implicitly includes both substituted and unsubstituted variants.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

Various embodiments are described by reference to chemical structures. In the chemical structures various chemical moieties are represented by R-groups. Some R-groups are described by reference to another chemical structure. A wavy bond line in a structure representing an R-group indicates the point at which the R-group is attached to or bonded to the main structure. In some chemical structures various cyclic moieties are represented by lettered rings. The lettered ring may represent a variety of cyclic structures. Some cyclic structures are described by reference to another chemical structure. A wavy bond line in a structure representing a cyclic structure indicates a bond that is shared with the main structure, or the point at which the cyclic structure is fused to the main structure to form a polycyclic structure. Various subscripts are also used. Each R-group has a numeric subscript which distinguishes it from other R-groups. R-groups and lettered rings may also include a lowercase alphabetical subscript, indicating that different embodiments, may have differing numbers of that moiety. If a lowercase alphabetical subscript may be 0, it means that, in some embodiments, the moiety may not be present. A dashed line in a cyclic structure indicates that in various embodiments one or more double-bounds may be present. When a compound may include more than one instance of a moiety, for example a moiety represented by an R-group, and that moiety is described as being "independently selected" from a list of options, each instance may be selected from the complete list without respect to any prior selections from the list; in other words, the instances may be the same or different and the same list item may be selected for multiple instances. Some R-group substitutions indicate a range, such as $C_1$-$C_6$ alkyl. Such a range indicates that the R-group may be a $C_1$ alkyl, a $C_2$ alkyl, a $C_3$ alkyl, a $C_4$ alkyl, a C$_5$ alkyl, or a C$_6$ alkyl. In other words, all such ranges are intended to include an explicit reference to each member within the range.

Overview

The 5'-nucleotidase, cytosolic II (NT5C2) gene (a protein coding gene) encodes cytosolic purine 5-nucleotidase, a 64,970 Da (561 amino acids) hydrolase that is located in the cytoplasmic matrix of cells and acts primarily on inosine 5'-monophosphate (IMP) and other purine nucleotides as a homotetramer. Purine 5-prime-nucleotidase is allosterically activated by various compounds, including ATP. It therefore has a role in purine metabolism, including maintaining proper ratios and quantities of intracellular purine and pyrimidine nucleotides, acting in cooperation with other nucleotidases. This gene also is responsible for the inactivation of nucleoside-analog chemotherapy drugs in about 19% of relapse T cell acute lymphoblastic leukemia (ALL) cells and about 3% of relapse B-precursor ALLs. Additional information on this gene is available in Tzoneva et al., "Activating mutations in the NT5C2 nucleotidase gene drive chemotherapy resistance in relapsed ALL." Nat. Med. 19(3): 368-371, 2013, which is hereby incorporated by reference in its entirety.

Acute lymphoblastic leukemia (ALL) is an aggressive hematological tumor resulting from the malignant transformation of lymphoid progenitors, which requires treatment with intensive chemotherapy. Despite much effort over the last decades, cure rates remain suboptimal, making relapsed ALL the fourth most frequent malignancy in children. Moreover, relapsed ALL is frequently associated with chemotherapy resistance and, despite salvage therapy with intensified treatment, cure rates are still unsatisfactory low. This is particularly the case in patients with relapsed T-ALL and in cases with primary resistance or early relapse, which is associated with higher risk of failure to achieve a second complete remission, shorter duration of chemotherapy response and poor survival. As result, relapsed ALL is still the leading cause of pediatric cancer associated death.

Multiple mechanisms have been implicated as drivers of relapse and resistance in ALL. Thus, leukemia initiating cells with stem cell properties including intrinsic self-renewal capacity and increased resistance to chemotherapy have been proposed to function as drivers of disease progression and relapse. In addition, protective niches in the bone marrow microenvironment may allow ALL cells to escape the cytotoxic effects of chemotherapy. Finally, clonal heterogeneity at diagnosis and genetic Darwinian evolution driven by the selective pressure of chemotherapy has been proposed to result in the emergence of leukemia clones harboring specific mutations driving chemotherapy resistance at the time of relapse. Thus, mapping the genetic landscape of relapse leukemias, defining the mechanism of action of relapse-associated mutations and developing effective strategies to reverse chemotherapy resistance have become major research imperatives in the field.

The NT5C2 gene product is a 5'-nucleotidase enzyme responsible for the dephosphorylation of metabolic intermediates in the salvage pathway of purine biosynthesis (IMP, XMP, GMP) and catalyzes a critical step for their export out of the cell in the form of inosine, xanthosine and guanosine. The nucleotidase activity of NT5C2 is tightly regulated. In basal conditions (the absence of allosteric activators), this enzyme adopts an inactive configuration. It is only activated upon interaction with positive allosteric regulators (e.g., ATP, ADP, Ap4A), which induce conformational changes that make the active center accessible to its substrates and competent for catalysis. However, the specific molecular mechanisms by which relapse-associated NT5C2 mutations trigger constitutively active NT5C2 nucleotidase activity remain to be elucidated.

Mechanistically, relapse-associated NT5C2 mutant proteins show increased nucleotidase activity in vitro and increased sensitivity to allosteric activators. In addition, and of utmost importance in the context of ALL therapy, NT5C2 mutations enhance the capacity of leukemic lymphoblasts to dephosphorylate and clear thio-IMP, thio-XMP and thio-GMP, the active cytotoxic metabolites of the thiopurine nucleoside analogs 6-mercaptopurine (6-MP) and 6-thioguanine (6-TG), two drugs broadly used in the treatment of ALL. Consistently, relapse-associated NT5C2 mutations confer selective resistance to 6-MP and 6-TG chemotherapy in ALL lymphoblasts.

NT5C2 mutant proteins show increased nucleotidase activity in vitro and confer resistance to chemotherapy with 6-mercaptopurine and 6-thioguanine when expressed in ALL lymphoblasts. These results support a prominent role for activating mutations in NT5C2 and increased nucleoside-analog metabolism in disease progression and chemotherapy resistance in ALL.

NT5C2 mutations result in increased enzymatic activity and drive resistance to thiopurine nucleoside analogs by decreasing the intracellular levels of active cytotoxic metabolites mediating the antileukemic effects of these drugs. Identifying activating mutations in NT5C2 as major drivers of chemotherapy resistance in 20% of relapsed ALLs (NT5C2 mutations are the single most recurrent genetic alteration acquired in relapsed lymphoblastic leukemia and are specifically associated with early relapse and progression under treatment) have provided a method to locate sites for interaction with NT5C2 inhibitors. NT5C2 inhibitors that modulate or reduce the activity of NT5C2 mutations can be used for the reversal of thiopurine resistance in relapsed ALL, including the preferred compounds described herein.

Enzymatic and structural analyses of NT5C2 mutant proteins, identified three distinct functional classes of relapse associated NT5C2 mutations. Each of these groups of mutations lock the NT5C2 protein in an active state, either by forcing a constitutively active configuration similar to that induced by allosteric activators, or via disruption of intramolecular switch-off mechanisms responsible for terminating activation and returning the enzyme to its resting inactive state. In this context, structure-function analysis of NT5C2 mutant proteins provided important new mechanistic insights on the mode of action of these mutations and support that small molecules interfering with allosteric activation can be active against the majority of NT5C2 mutant proteins. Two families of active small molecule NT5C2 inhibitors have been identified, as well as a core structure for binding to NT5C2.

General Discussion

Compounds

Various embodiments relate to the synthesis and characterization of NT5C2 inhibitors, HTP47 and HTP48, for treatment of chemotherapy resistant T-ALL. HTP47 and HTP48 demonstrated NT5C2 inhibitory activity in a malachite green based assay, an in vitro screening method based on detection of free inorganic phosphate. In a dose-dependent manner, HTP47 and HTP48 act synergistically with 6-mercaptopurine (6-MP),

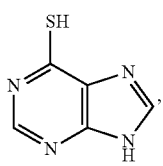

to decrease cell viability of NT5C2 R367Q mutant mouse lymphoblasts. As such, various embodiments may be used in combination with existing chemotherapies to treat T-ALL and relapsed T-ALL.

Various embodiments relate to ongoing in vitro and in vivo functional characterization and development of optimized inhibitors. Various compounds were tested for NT5C2 inhibitory activity. The tests indicated that HTP2, HTP47, HTP48, HTP41, HTP22 have NT5C2 inhibitory activity. The tests demonstrate NT5C2 inhibitory activity for HTP2, HTP47, HTP48 using a malachite green based assay. Control experiment were performed for dose optimization of HTP47 and HTP48 in C2-2 NT5C2 WT mouse lymphoblasts. It was unexpectedly discovered that HTP47 and HTP48 act synergistically with 6-MP in a dose-dependent manner to decrease cell viability of NT5C2 R367Q mutant mouse lymphoblasts. This indicates greater potency of 6-MP in combination with HTP47 compared to HTP48. Synthesis reactions for HTP47 and HTP48 are also provided.

Various embodiments have applications in therapies for T-ALL and ALL, for treatment of relapsed T-ALL and ALL in combination with chemotherapy, as prophylactic to prevent chemotherapy resistance in T-ALL and ALL, and as treatment for other disorders with gain of function mutations in NT5C2.

Various embodiments relate to a compound, having the structure:

Structure A

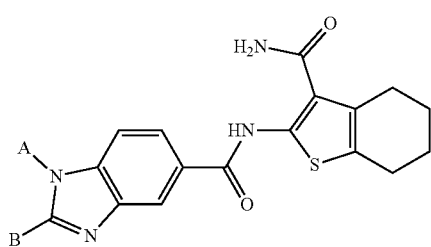

According to various embodiments A and B may be any suitable substituent. For example, according to various embodiments, A may be selected from hydrogen and methyl and B may be selected from hydrogen and methyl.

Various embodiments relate to a compound, having the structure:

Structure B

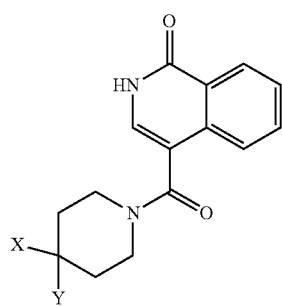

According to various embodiments X and Y may be any suitable substituent. For example, according to various embodiments, X may be selected from hydrogen and

and Y may be selected from the group consisting of

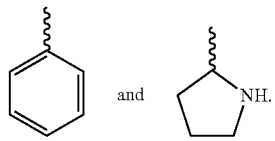

The compound according to various embodiments may inhibit NT5C2 nucleotidase. The compounds according to various embodiments may synergistically decrease cell viability of NT5C2 R367Q mutant lymphoblasts when used in combination with 6-mercaptopurine (6-MP) to treat a cancer. The cancer may be, but is not limited to, acute lymphoblastic leukemia.

Various embodiments relate to a composition comprising a compound according to any embodiment described herein or a pharmaceutically acceptable salt or derivative thereof and a pharmaceutically acceptable carrier.

Various embodiments relate to methods of treating cancer. The method may comprise administering a therapeutically effective amount of a compound according to any embodiment described herein or a pharmaceutically acceptable salt or derivative thereof. The compound may be administered by any suitable technique. The cancer may be, but is not limited to, acute lymphoblastic leukemia.

FIG. 1 is an example according to various embodiments, illustrating the NT5C2 inhibition response for varying amounts (μM) of a compound according to Formula 1 (HTP_2).

Formula 1 (HTP_2)

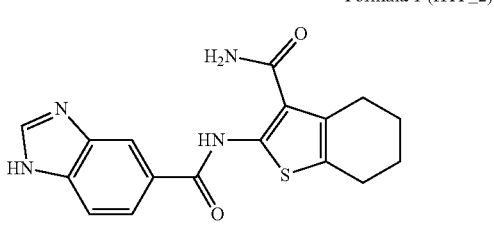

According to various embodiments, HTP_2, as shown in Formula 1 may be synthesized according to Reaction Scheme 1. Those skilled in the art are readily able to modify Reaction Scheme 1 without undue experimentation to arrive at the other compounds described herein, including the compounds depicted in Formulas 2-33.

Reaction Scheme 1

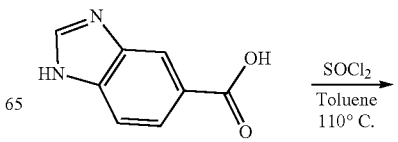

-continued

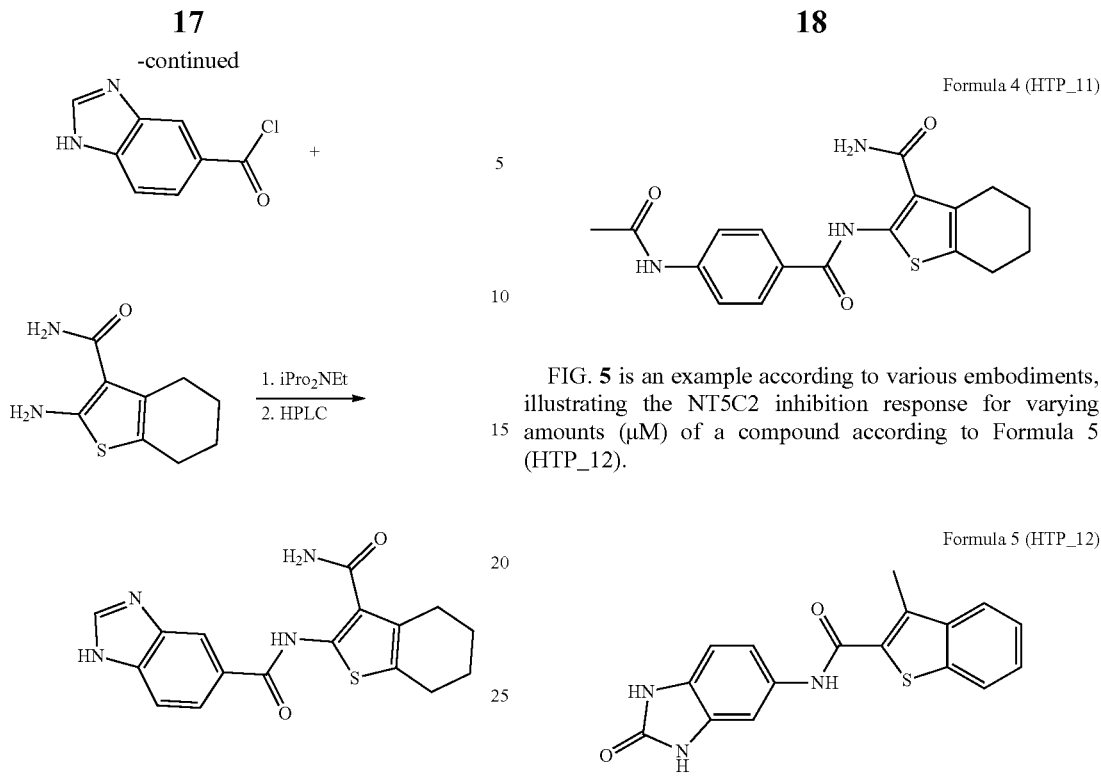

Figure 2:
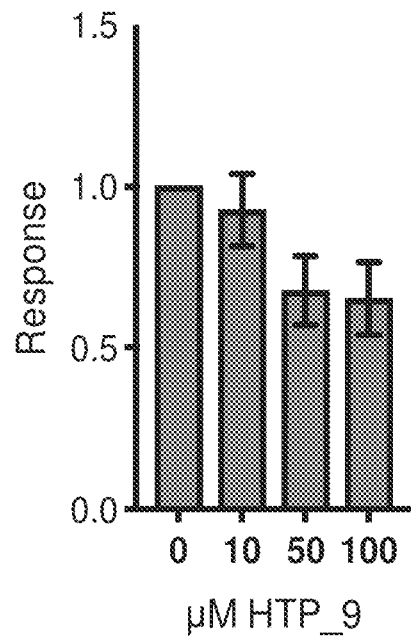
FIG. 2 is an example according to various embodiments, illustrating the NT5C2 inhibition response for varying amounts (μM) of a compound according to Formula 2 (HTP_9).

FIG. 2 is an example according to various embodiments, illustrating the NT5C2 inhibition response for varying amounts (µM) of a compound according to Formula 2 (HTP_9).

Formula 2 (HTP_9)

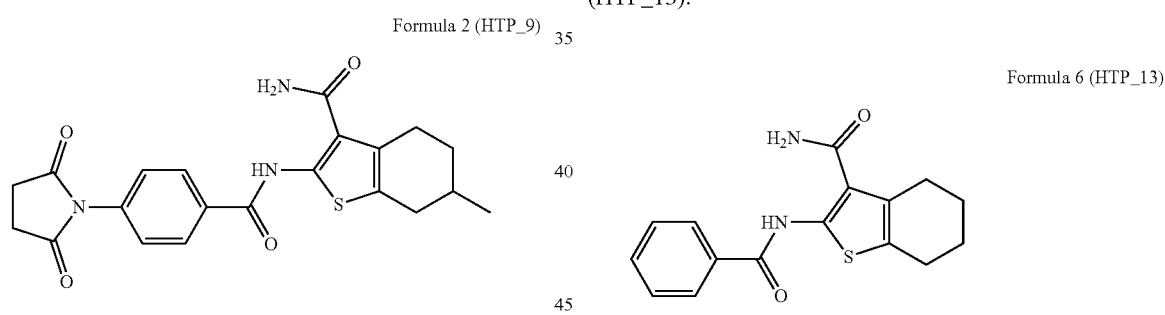

Figure 3:
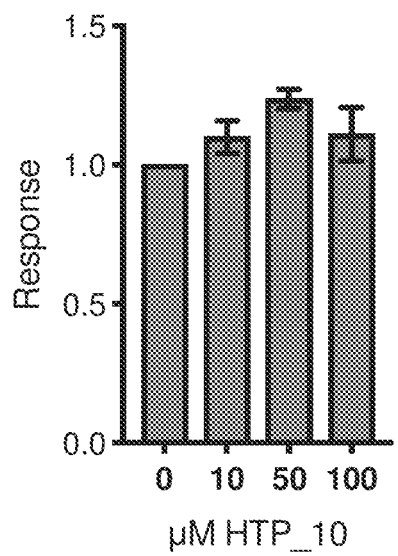
FIG. 3 is an example according to various embodiments, illustrating the NT5C2 inhibition response for varying amounts (μM) of a compound according to Formula 3 (HTP_10).

FIG. 3 is an example according to various embodiments, illustrating the NT5C2 inhibition response for varying amounts (µM) of a compound according to Formula 3 (HTP_10).

Formula 3 (HTP_10)

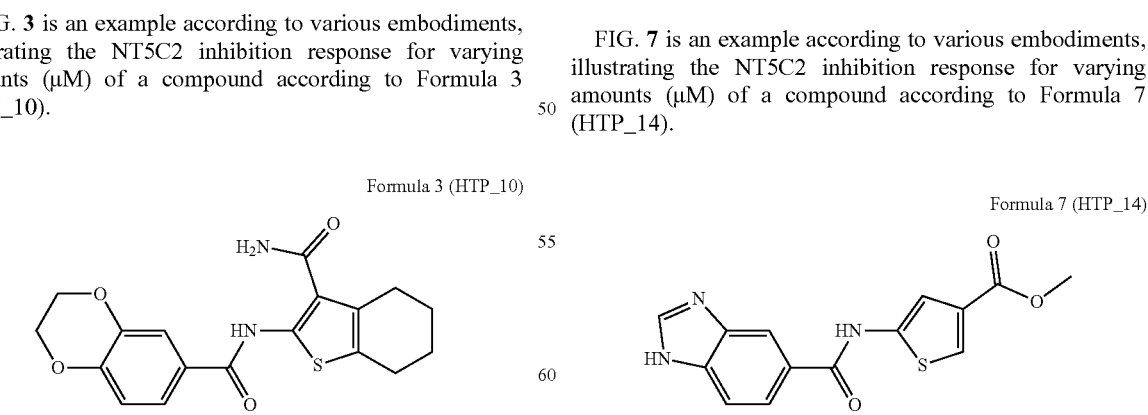

Figure 4:
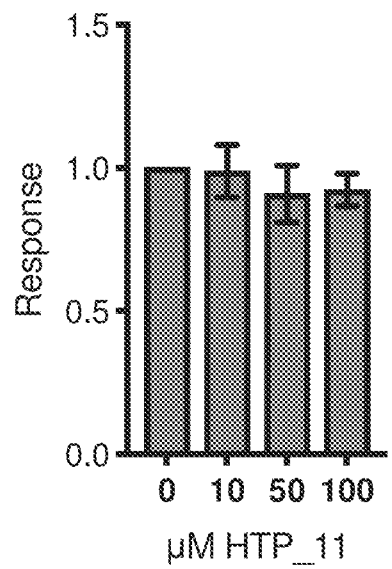
FIG. 4 is an example according to various embodiments, illustrating the NT5C2 inhibition response for varying amounts (μM) of a compound according to Formula 4 (HTP_11).

FIG. 4 is an example according to various embodiments, illustrating the NT5C2 inhibition response for varying amounts (µM) of a compound according to Formula 4 (HTP_11).

Formula 4 (HTP_11)

Figure 5:
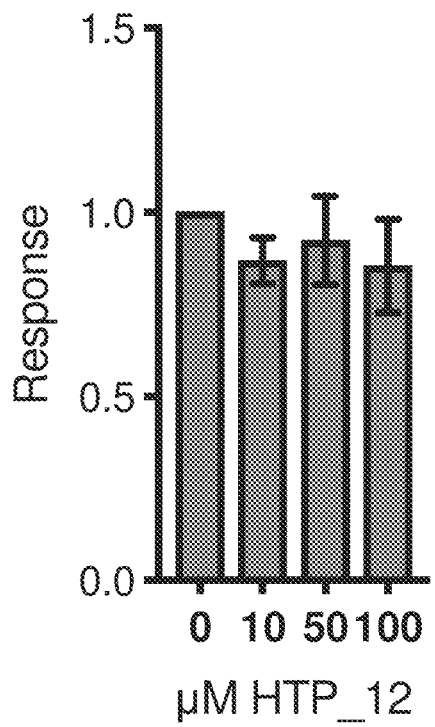
FIG. 5 is an example according to various embodiments, illustrating the NT5C2 inhibition response for varying amounts (μM) of a compound according to Formula 5 (HTP_12).

FIG. 5 is an example according to various embodiments, illustrating the NT5C2 inhibition response for varying amounts (µM) of a compound according to Formula 5 (HTP_12).

Formula 5 (HTP_12)

Figure 6:
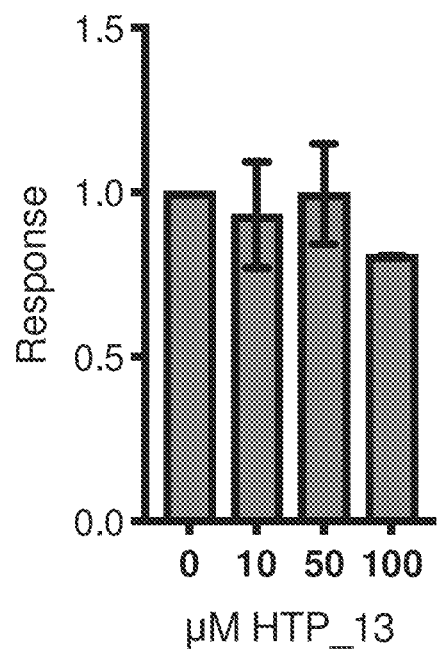
FIG. 6 is an example according to various embodiments, illustrating the NT5C2 inhibition response for varying amounts (μM) of a compound according to Formula 6 (HTP_13).

FIG. 6 is an example according to various embodiments, illustrating the NT5C2 inhibition response for varying amounts (µM) of a compound according to Formula 6 (HTP_13).

Formula 6 (HTP_13)

Figure 7:
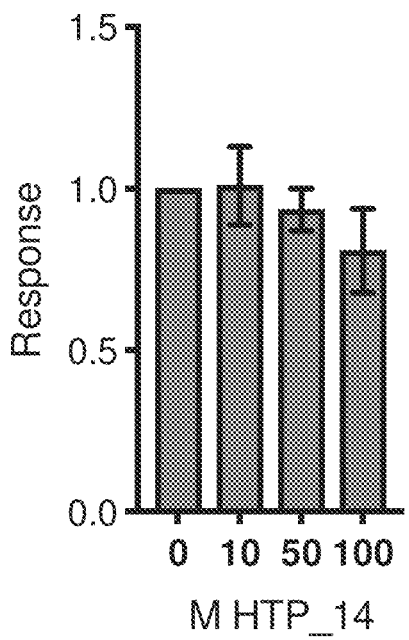
FIG. 7 is an example according to various embodiments, illustrating the NT5C2 inhibition response for varying amounts (μM) of a compound according to Formula 7 (HTP_14).

FIG. 7 is an example according to various embodiments, illustrating the NT5C2 inhibition response for varying amounts (µM) of a compound according to Formula 7 (HTP_14).

Formula 7 (HTP_14)

Figure 8:
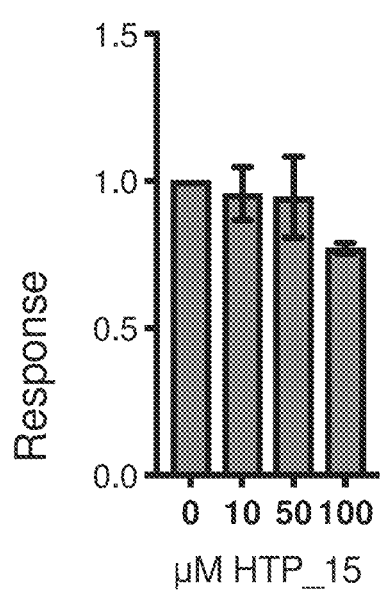
FIG. 8 is an example according to various embodiments, illustrating the NT5C2 inhibition response for varying amounts (μM) of a compound according to Formula 8 (HTP_15).

FIG. 8 is an example according to various embodiments, illustrating the NT5C2 inhibition response for varying amounts (µM) of a compound according to Formula 8 (HTP_15).

Formula 8 (HTP_15)

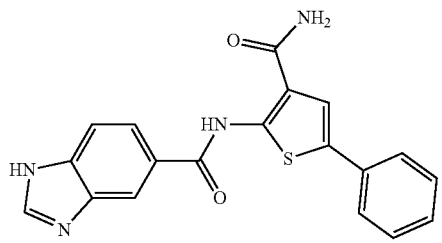

Figure 9:
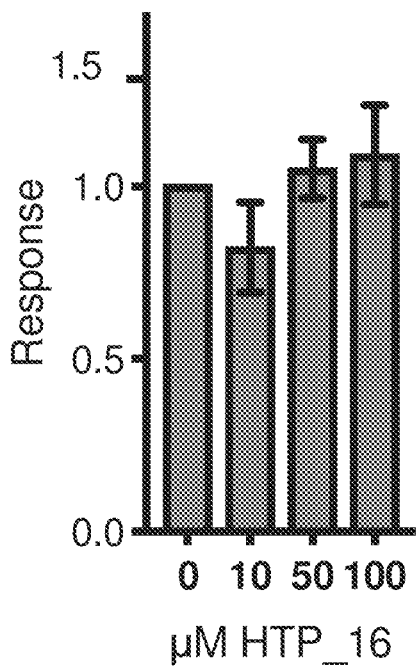
FIG. 9 is an example according to various embodiments, illustrating the NT5C2 inhibition response for varying amounts (μM) of a compound according to Formula 9 (HTP_16).

FIG. 9 is an example according to various embodiments, illustrating the NT5C2 inhibition response for varying amounts (μM) of a compound according to Formula 9 (HTP_16).

Formula 9 (HTP_16)

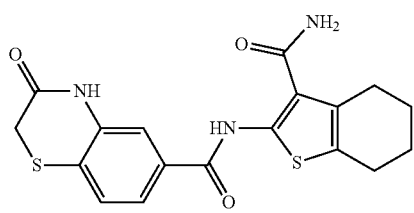

Figure 10:
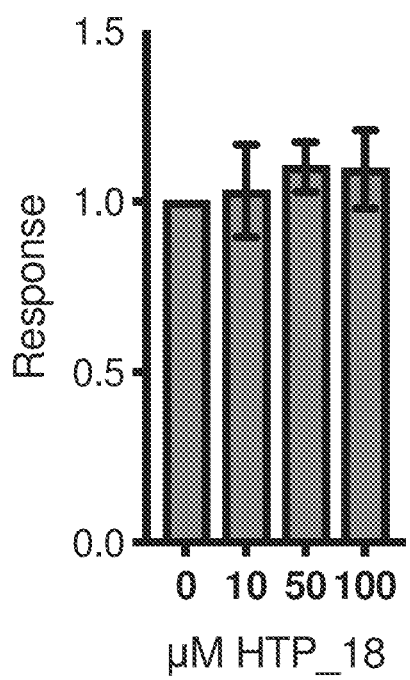
FIG. 10 is an example according to various embodiments, illustrating the NT5C2 inhibition response for varying amounts (μM) of a compound according to Formula 10 (HTP_18).

FIG. 10 is an example according to various embodiments, illustrating the NT5C2 inhibition response for varying amounts (μM) of a compound according to Formula 10 (HTP_18).

Formula 10 (HTP_18)

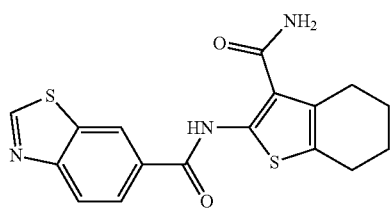

Figure 11:
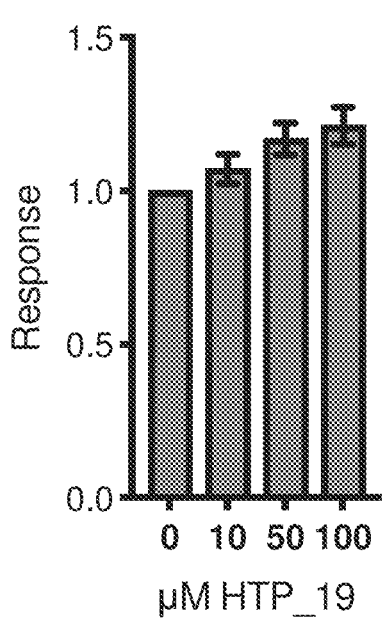
FIG. 11 is an example according to various embodiments, illustrating the NT5C2 inhibition response for varying amounts (μM) of a compound according to Formula 11 (HTP_19).

FIG. 11 is an example according to various embodiments, illustrating the NT5C2 inhibition response for varying amounts (μM) of a compound according to Formula 11 (HTP_19).

Formula 11 (HTP_19)

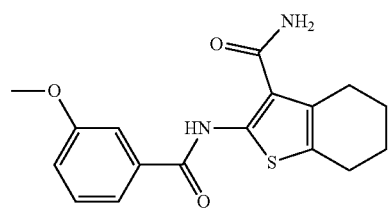

Figure 12:
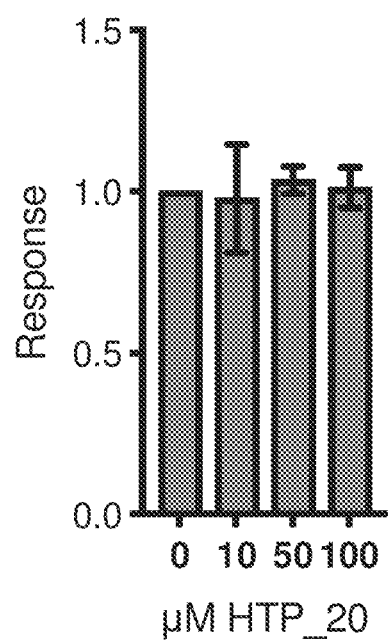
FIG. 12 is an example according to various embodiments, illustrating the NT5C2 inhibition response for varying amounts (μM) of a compound according to Formula 12 (HTP_20).

FIG. 12 is an example according to various embodiments, illustrating the NT5C2 inhibition response for varying amounts (μM) of a compound according to Formula 12 (HTP_20).

Formula 12 (HTP_20)

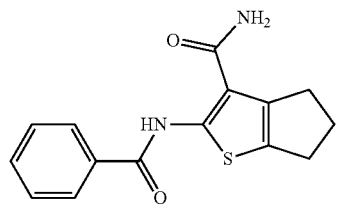

Figure 13:
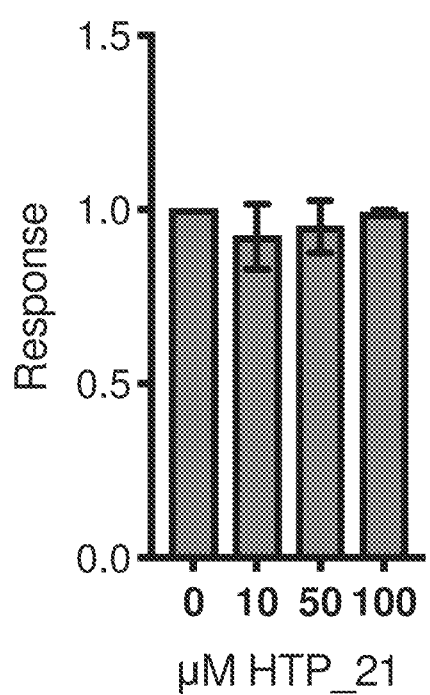
FIG. 13 is an example according to various embodiments, illustrating the NT5C2 inhibition response for varying amounts (μM) of a compound according to Formula 13 (HTP_21).

FIG. 13 is an example according to various embodiments, illustrating the NT5C2 inhibition response for varying amounts (μM) of a compound according to Formula 13 (HTP_21).

Formula 13 (HTP_21)

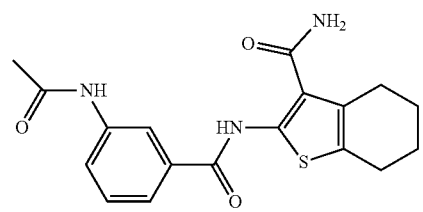

Figure 14:
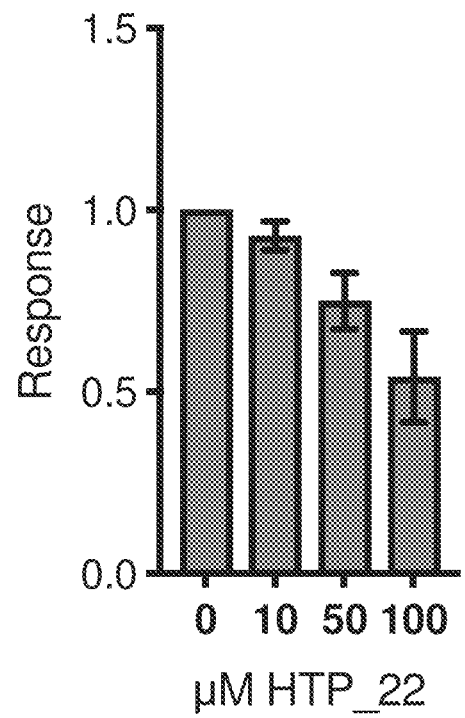
FIG. 14 is an example according to various embodiments, illustrating the NT5C2 inhibition response for varying amounts (μM) of a compound according to Formula 14 (HTP_22).

FIG. 14 is an example according to various embodiments, illustrating the NT5C2 inhibition response for varying amounts (μM) of a compound according to Formula 14 (HTP_22).

Formula 14 (HTP_22)

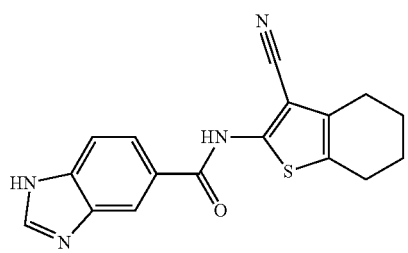

Figure 15:
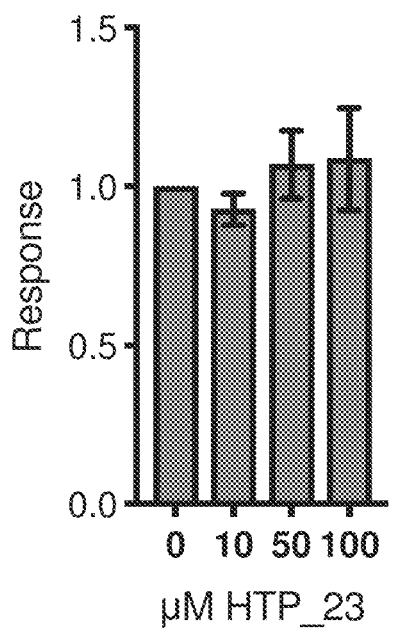
FIG. 15 is an example according to various embodiments, illustrating the NT5C2 inhibition response for varying amounts (μM) of a compound according to Formula 15 (HTP_23).

FIG. 15 is an example according to various embodiments, illustrating the NT5C2 inhibition response for varying amounts (μM) of a compound according to Formula 15 (HTP_23).

Formula 15 (HTP_23)

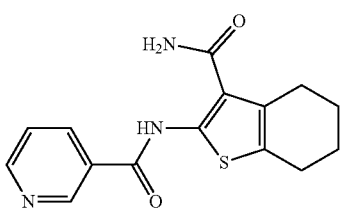

Figure 16:
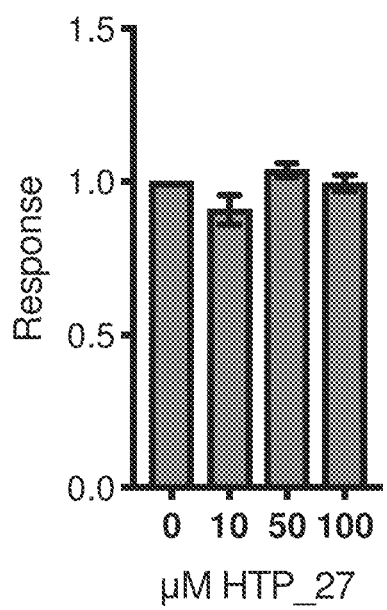
FIG. 16 is an example according to various embodiments, illustrating the NT5C2 inhibition response for varying amounts (μM) of a compound according to Formula 16 (HTP_27).

FIG. 16 is an example according to various embodiments, illustrating the NT5C2 inhibition response for varying amounts (μM) of a compound according to Formula 16 (HTP_27).

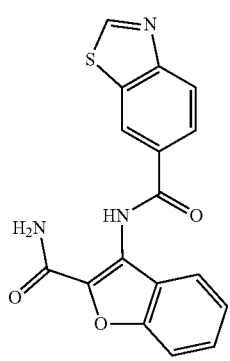

Formula 16 (HTP_27)

Figure 17:
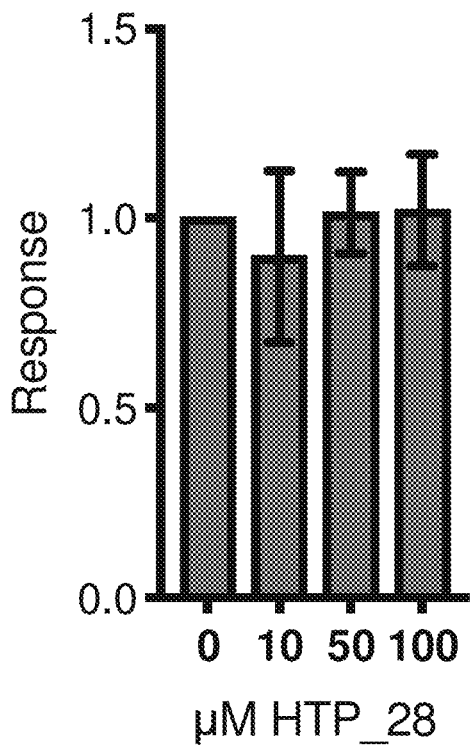
FIG. 17 is an example according to various embodiments, illustrating the NT5C2 inhibition response for varying amounts (μM) of a compound according to Formula 17 (HTP_28).

FIG. 17 is an example according to various embodiments, illustrating the NT5C2 inhibition response for varying amounts (μM) of a compound according to Formula 17 (HTP_28).

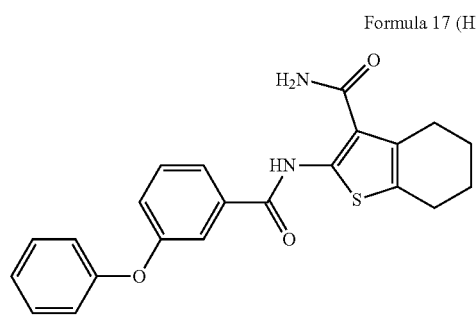

Formula 17 (HTP_28)

Figure 18:
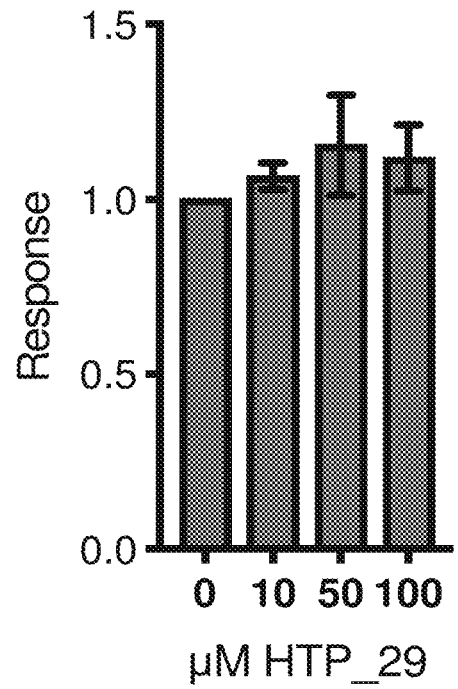
FIG. 18 is an example according to various embodiments, illustrating the NT5C2 inhibition response for varying amounts (μM) of a compound according to Formula 18 (HTP_29).

FIG. 18 is an example according to various embodiments, illustrating the NT5C2 inhibition response for varying amounts (μM) of a compound according to Formula 18 (HTP_29).

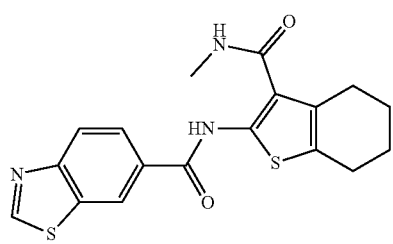

Formula 18 (HTP_29)

Figure 19:
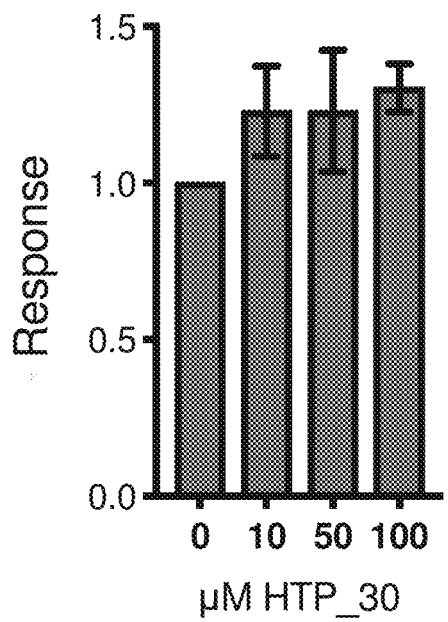
FIG. 19 is an example according to various embodiments, illustrating the NT5C2 inhibition response for varying amounts (μM) of a compound according to Formula 19 (HTP_30).

FIG. 19 is an example according to various embodiments, illustrating the NT5C2 inhibition response for varying amounts (μM) of a compound according to Formula 19 (HTP_30).

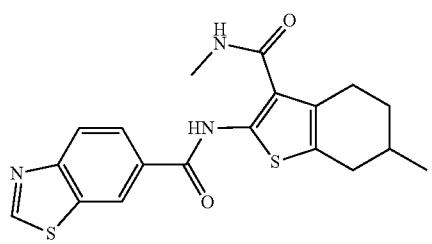

Formula 19 (HTP_30)

Figure 20:
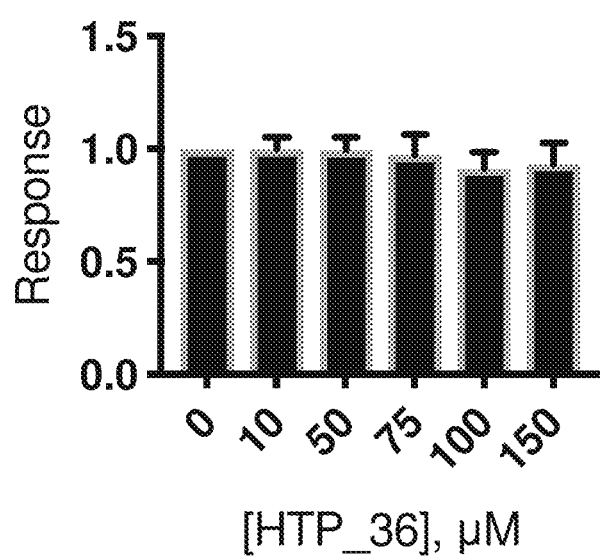
FIG. 20 is an example according to various embodiments, illustrating the NT5C2 inhibition response for varying amounts (μM) of a compound according to Formula 20 (HTP_36).

FIG. 20 is an example according to various embodiments, illustrating the NT5C2 inhibition response for varying amounts (μM) of a compound according to Formula 20 (HTP_36).

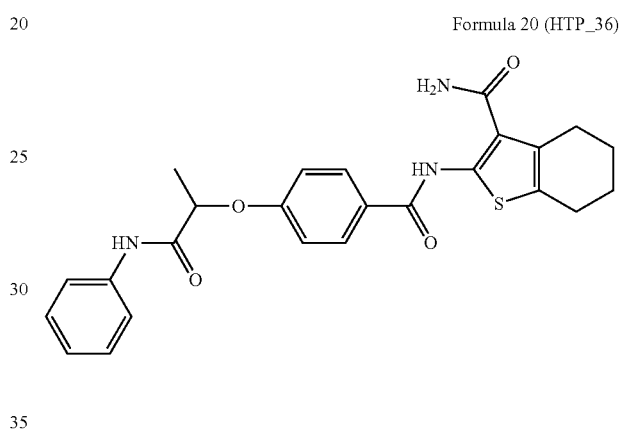

Formula 20 (HTP_36)

Figure 21:
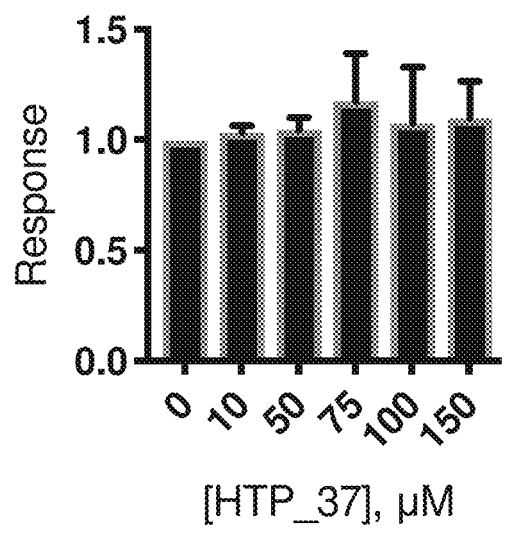
FIG. 21 is an example according to various embodiments, illustrating the NT5C2 inhibition response for varying amounts (μM) of a compound according to Formula 21 (HTP_37).

FIG. 21 is an example according to various embodiments, illustrating the NT5C2 inhibition response for varying amounts (μM) of a compound according to Formula 21 (HTP_37).

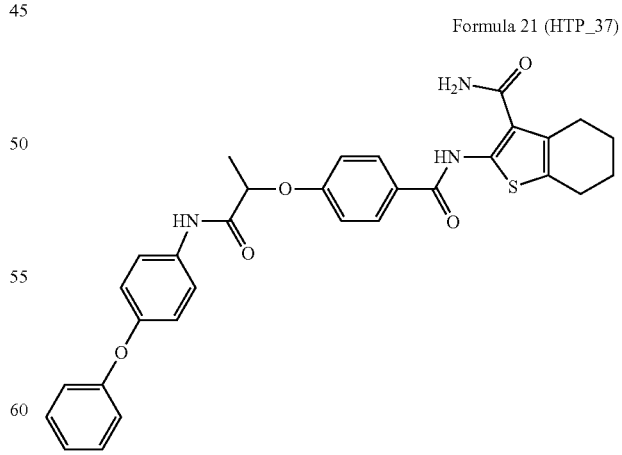

Formula 21 (HTP_37)

Figure 22:
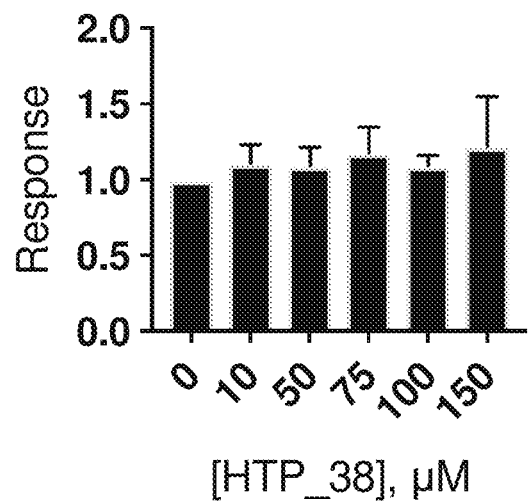
FIG. 22 is an example according to various embodiments, illustrating the NT5C2 inhibition response for varying amounts (μM) of a compound according to Formula 22 (HTP_38).

FIG. 22 is an example according to various embodiments, illustrating the NT5C2 inhibition response for varying amounts (μM) of a compound according to Formula 22 (HTP_38).

Formula 22 (HTP_38)

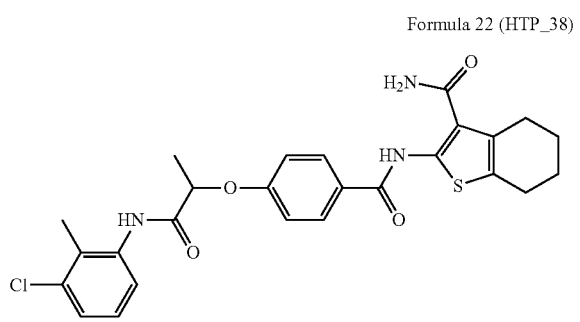 [SMILES: Cc1c(Cl)cccc1NC(=O)C(C)Oc1ccc(C(=O)Nc2sc3c(c2C(N)=O)CCCC3)cc1]

Figure 23:
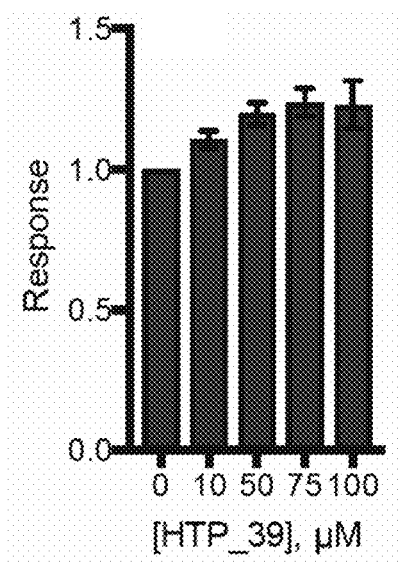
FIG. 23 is an example according to various embodiments, illustrating the NT5C2 inhibition response for varying amounts (μM) of a compound according to Formula 23 (HTP_39).

FIG. 23 is an example according to various embodiments, illustrating the NT5C2 inhibition response for varying amounts (μM) of a compound according to Formula 23 (HTP_39).

Formula 23 (HTP_39)

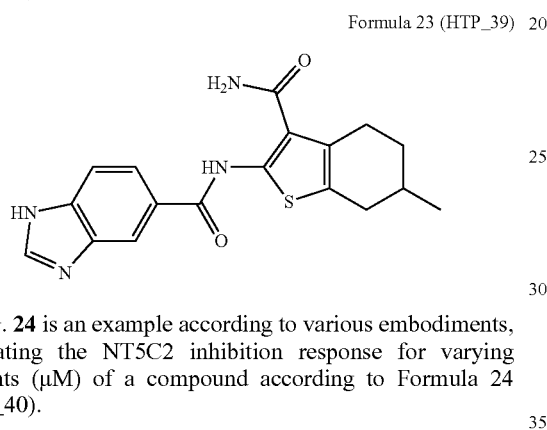

Figure 24:
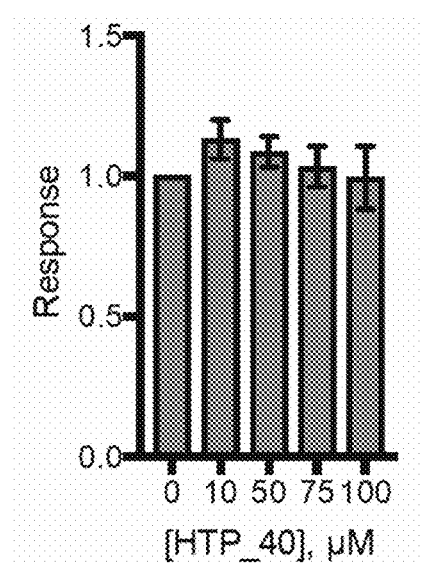
FIG. 24 is an example according to various embodiments, illustrating the NT5C2 inhibition response for varying amounts (μM) of a compound according to Formula 24 (HTP_40).

FIG. 24 is an example according to various embodiments, illustrating the NT5C2 inhibition response for varying amounts (μM) of a compound according to Formula 24 (HTP_40).

Formula 24 (HTP_40)

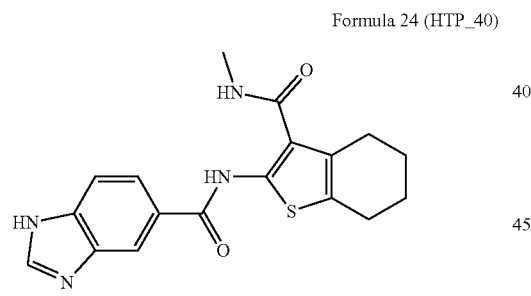

Figure 25:
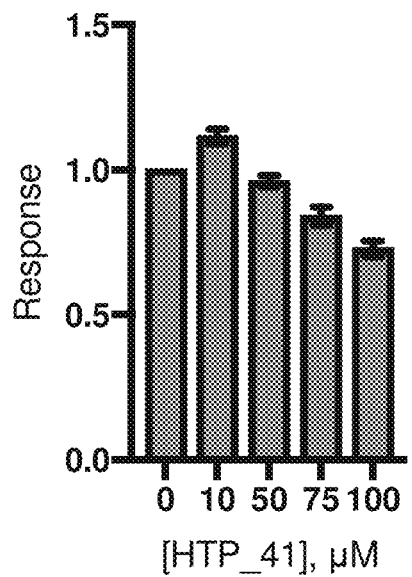
FIG. 25 is an example according to various embodiments, illustrating the NT5C2 inhibition response for varying amounts (μM) of a compound according to Formula 25 (HTP_41).

FIG. 25 is an example according to various embodiments, illustrating the NT5C2 inhibition response for varying amounts (μM) of a compound according to Formula 25 (HTP_41).

Formula 25 (HTP_41)

Figure 26:
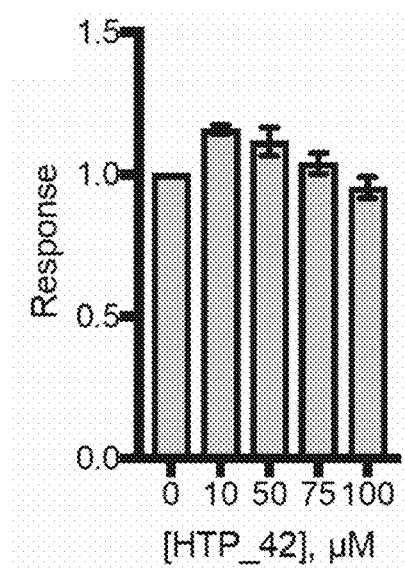
FIG. 26 is an example according to various embodiments, illustrating the NT5C2 inhibition response for varying amounts (μM) of a compound according to Formula 26 (HTP_42).

FIG. 26 is an example according to various embodiments, illustrating the NT5C2 inhibition response for varying amounts (μM) of a compound according to Formula 26 (HTP_42).

Formula 26 (HTP_42)

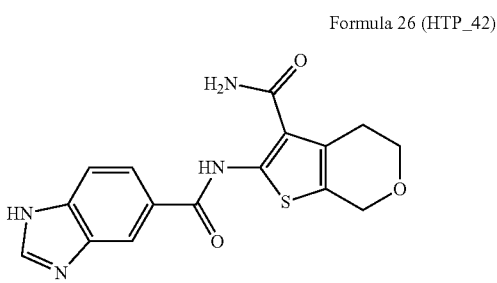 [SMILES: NC(=O)c1c(NC(=O)c2ccc3[nH]cnc3c2)sc2c1CCOC2]

Figure 27:
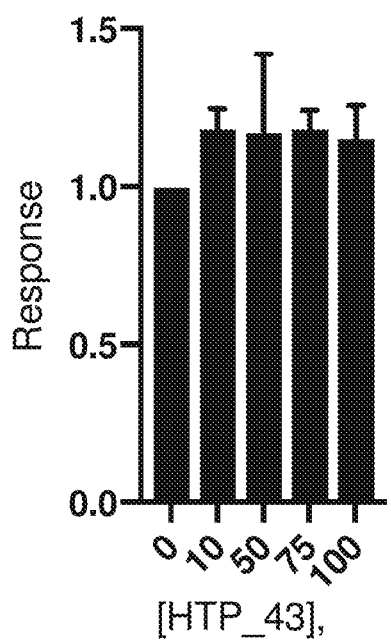
FIG. 27 is an example according to various embodiments, illustrating the NT5C2 inhibition response for varying amounts (μM) of a compound according to Formula 27 (HTP_43).

FIG. 27 is an example according to various embodiments, illustrating the NT5C2 inhibition response for varying amounts (μM) of a compound according to Formula 27 (HTP_43).

Formula 27 (HTP_43)

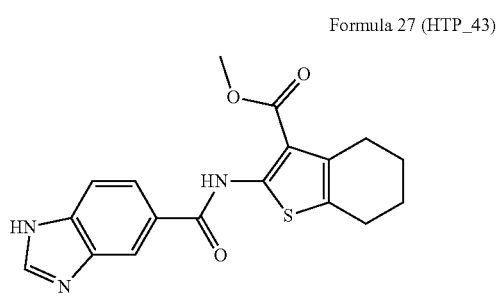 [SMILES: COC(=O)c1c(NC(=O)c2ccc3[nH]cnc3c2)sc2c1CCCC2]

Figure 28:
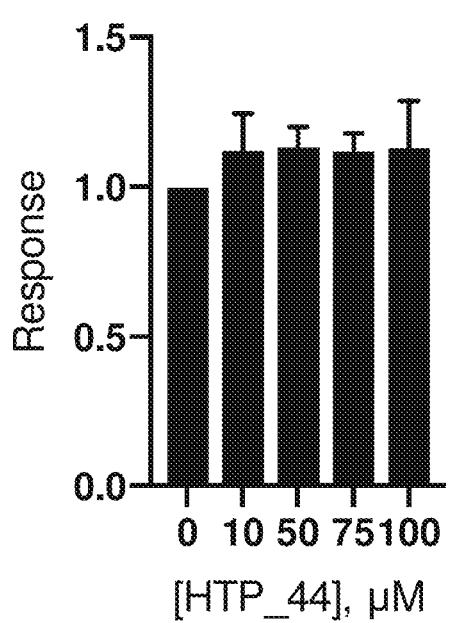
FIG. 28 is an example according to various embodiments, illustrating the NT5C2 inhibition response for varying amounts (μM) of a compound according to Formula 28 (HTP_44).

FIG. 28 is an example according to various embodiments, illustrating the NT5C2 inhibition response for varying amounts (μM) of a compound according to Formula 28 (HTP_44).

Formula 28 (HTP_44)

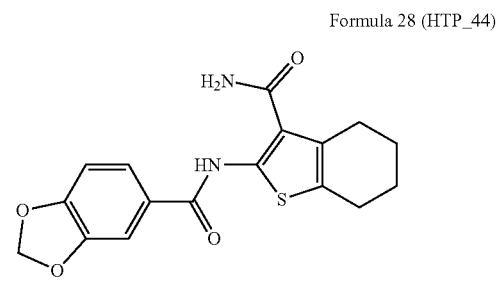 [SMILES: NC(=O)c1c(NC(=O)c2ccc3c(c2)OCO3)sc2c1CCCC2]

Figure 29:
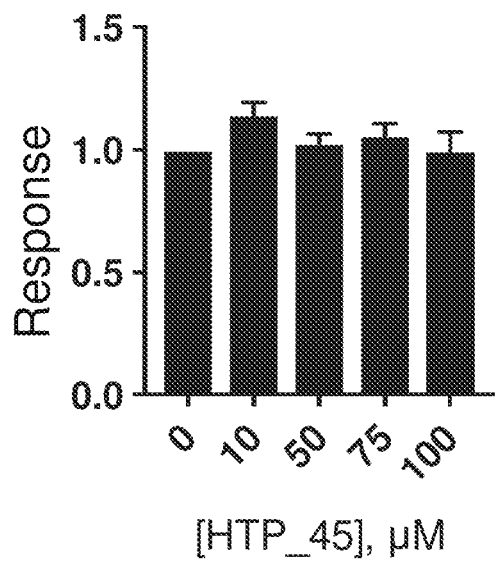
FIG. 29 is an example according to various embodiments, illustrating the NT5C2 inhibition response for varying amounts (μM) of a compound according to Formula 29 (HTP_45).

FIG. 29 is an example according to various embodiments, illustrating the NT5C2 inhibition response for varying amounts (μM) of a compound according to Formula 29 (HTP_45).

Formula 29 (HTP_45)

Figure 30:
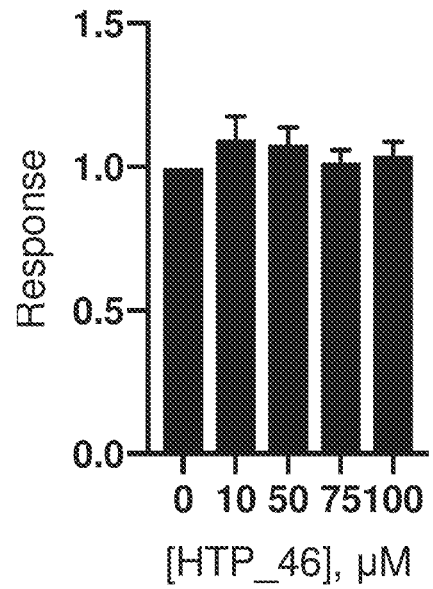
FIG. 30 is an example according to various embodiments, illustrating the NT5C2 inhibition response for varying amounts (μM) of a compound according to Formula 30 (HTP_46).

FIG. 30 is an example according to various embodiments, illustrating the NT5C2 inhibition response for varying amounts (μM) of a compound according to Formula 30 (HTP_46).

Formula 30 (HTP_46)

Figure 31:
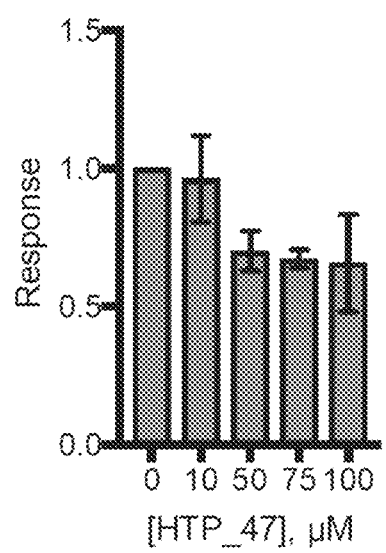
FIG. 31 is an example according to various embodiments, illustrating the NT5C2 inhibition response for varying amounts (μM) of a compound according to Formula 31 (HTP_47).

FIG. 31 is an example according to various embodiments, illustrating the NT5C2 inhibition response for varying amounts (μM) of a compound according to Formula 31 (HTP_47).

Formula 31 (HTP_47)

Figure 32:
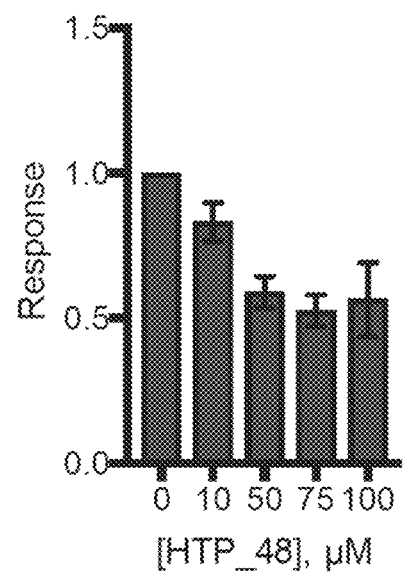
FIG. 32 is an example according to various embodiments, illustrating the NT5C2 inhibition response for varying amounts (μM) of a compound according to Formula 32 (HTP_48).

FIG. 32 is an example according to various embodiments, illustrating the NT5C2 inhibition response for varying amounts (μM) of a compound according to Formula 32 (HTP_48).

Formula 32 (HTP_48)

Figure 33:
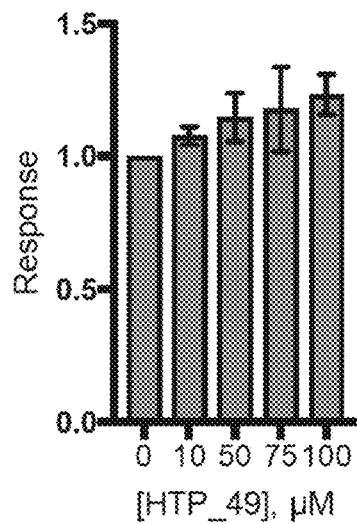
FIG. 33 is an example according to various embodiments, illustrating the NT5C2 inhibition response for varying amounts (μM) of a compound according to Formula 33 (HTP_49).
Figure 34A:
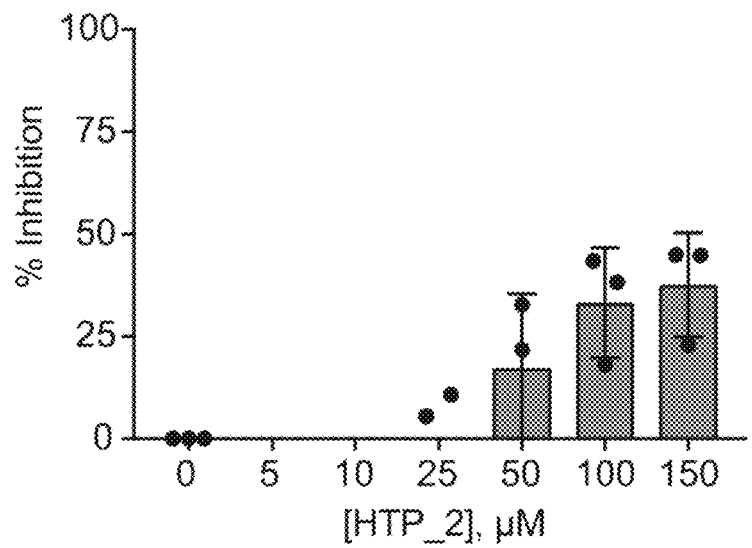
FIG. 34A through 34K are examples according to various embodiments, illustrating inhibition and reversal of 6-MP resistance in NT5C2 mutant acute lymphoblastic leukemia of compounds according to Formula 1 (HTP_2).
Figure 34B:
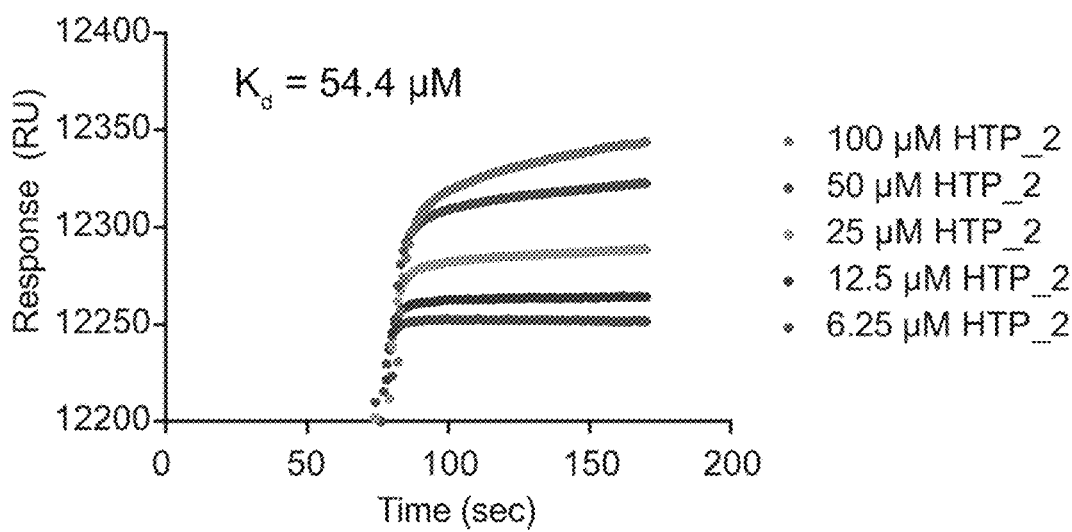
Figure 34C:
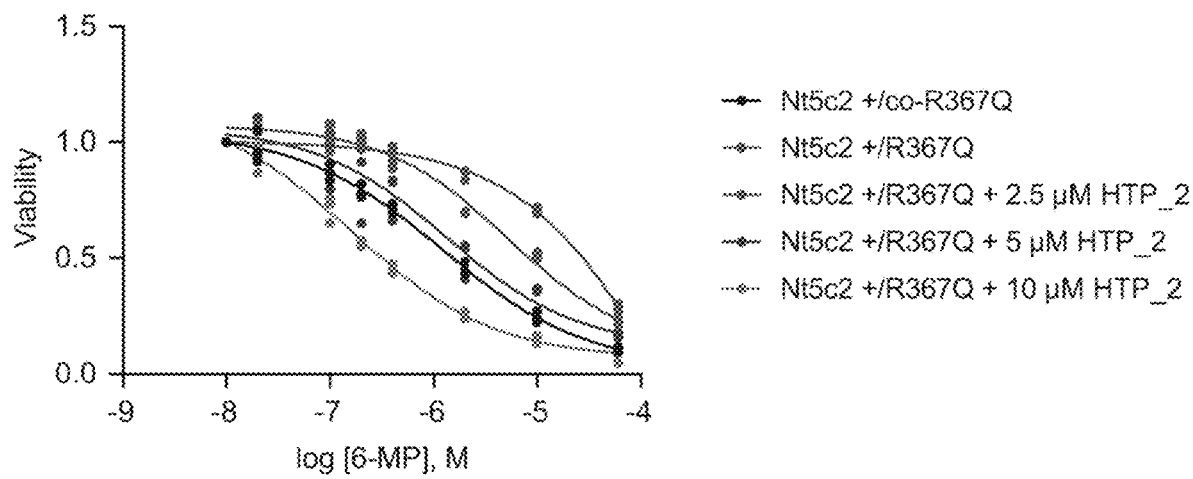
Figure 34D:
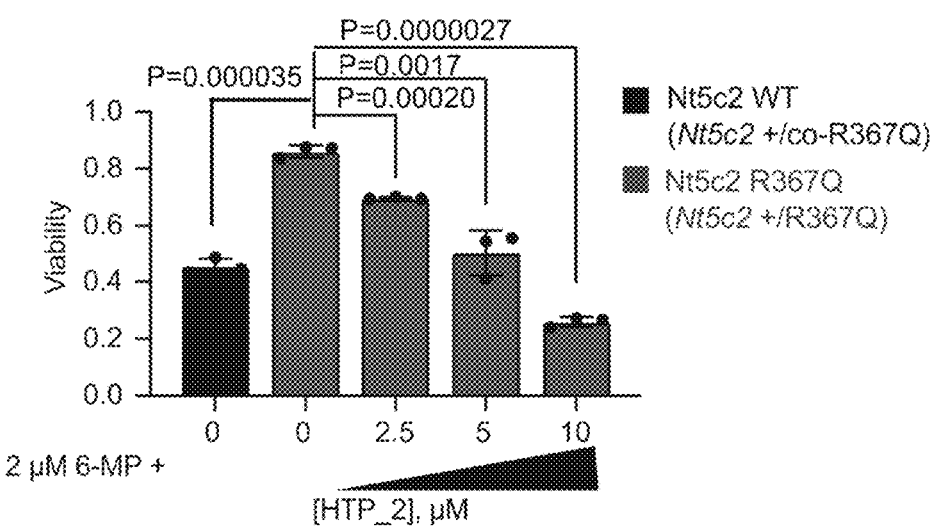
Figure 34E:
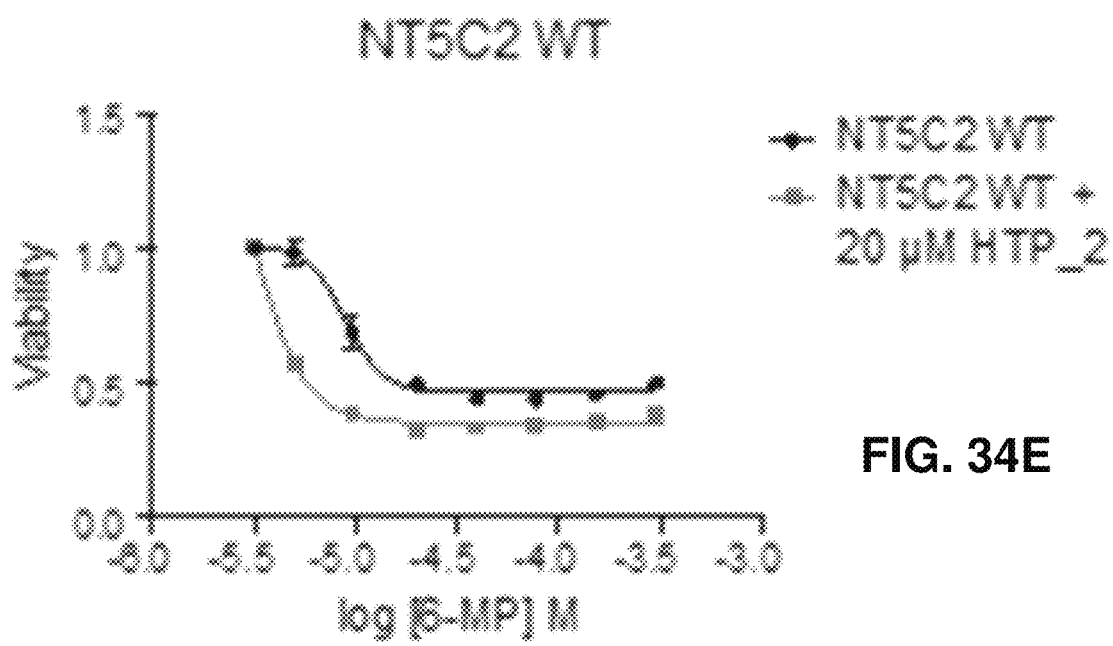
Figure 34F:
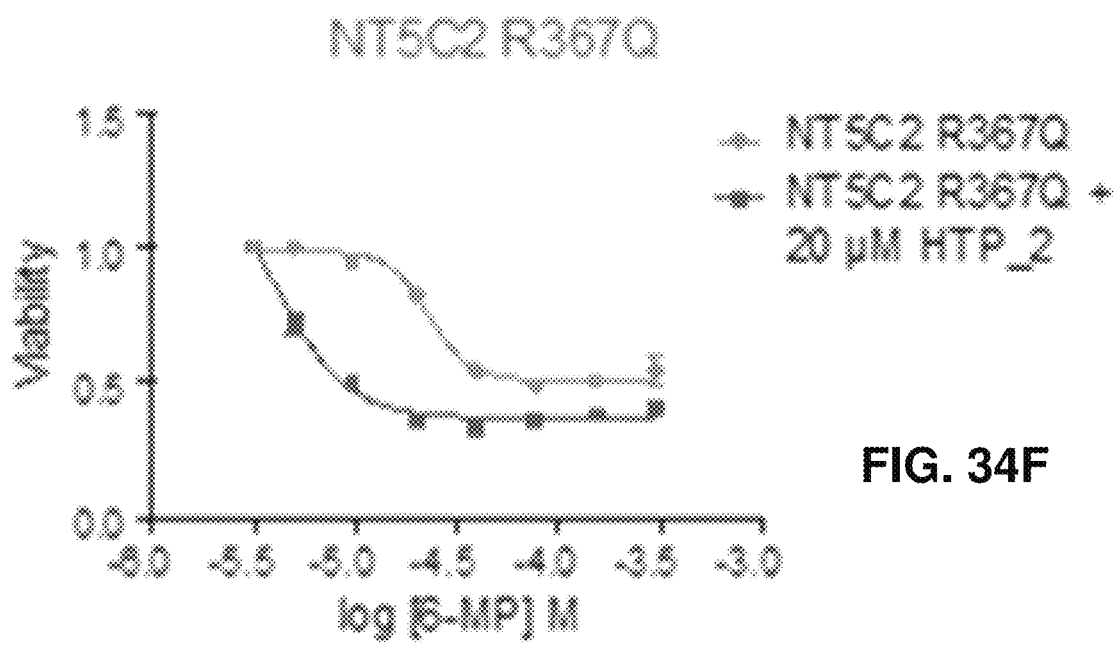
Figure 34G:
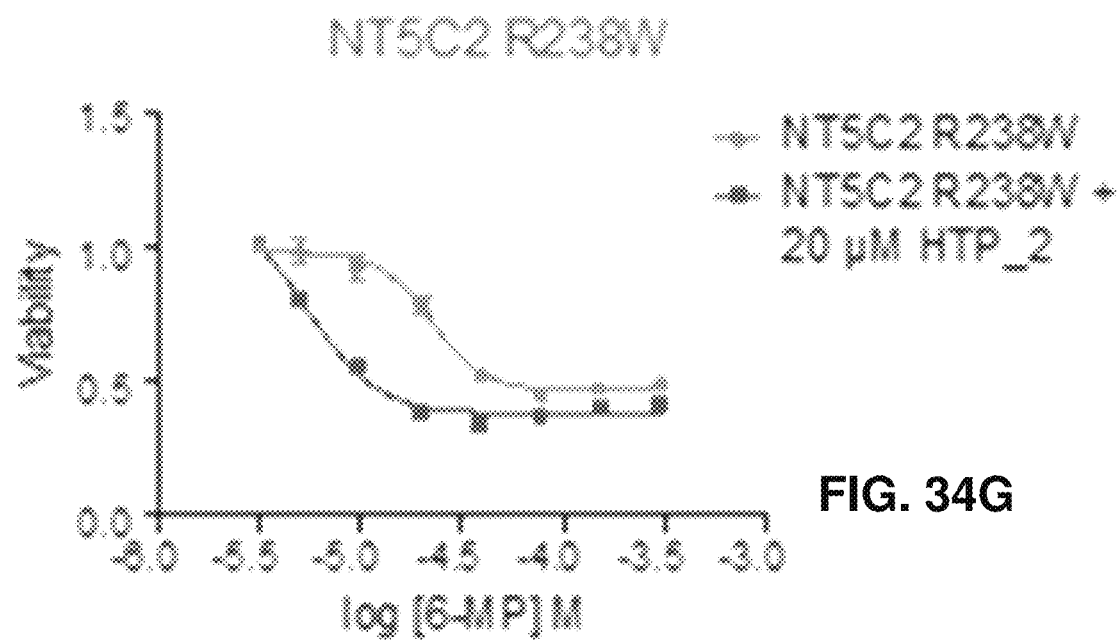
Figure 34H:
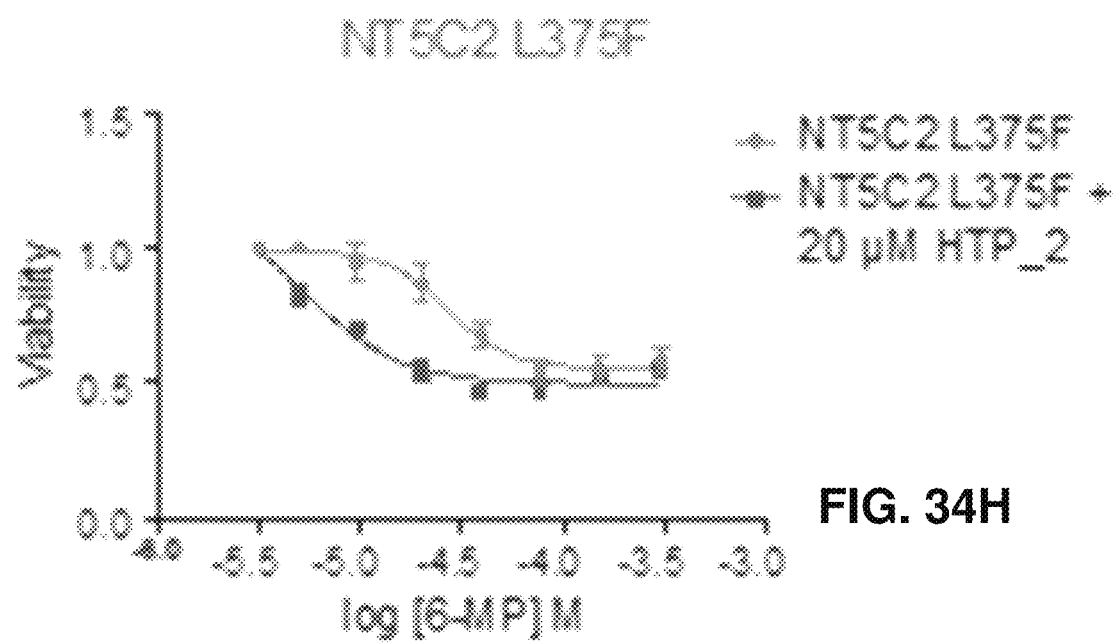
Figure 34I:
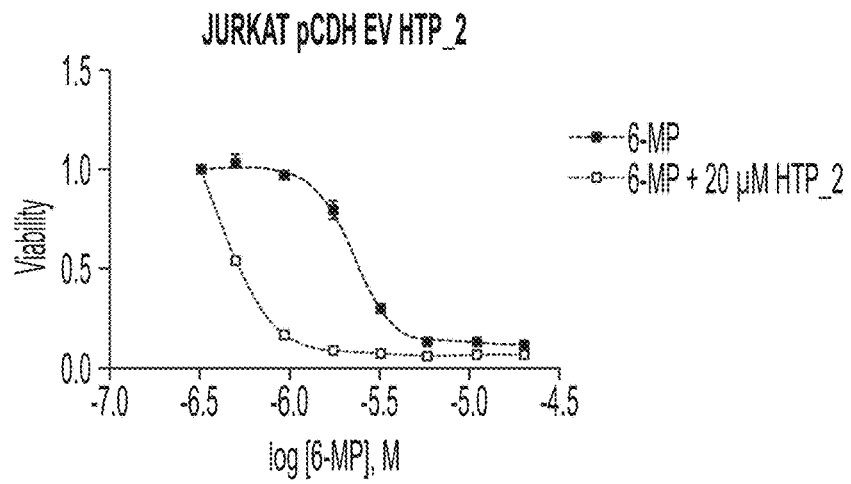
Figure 34J:
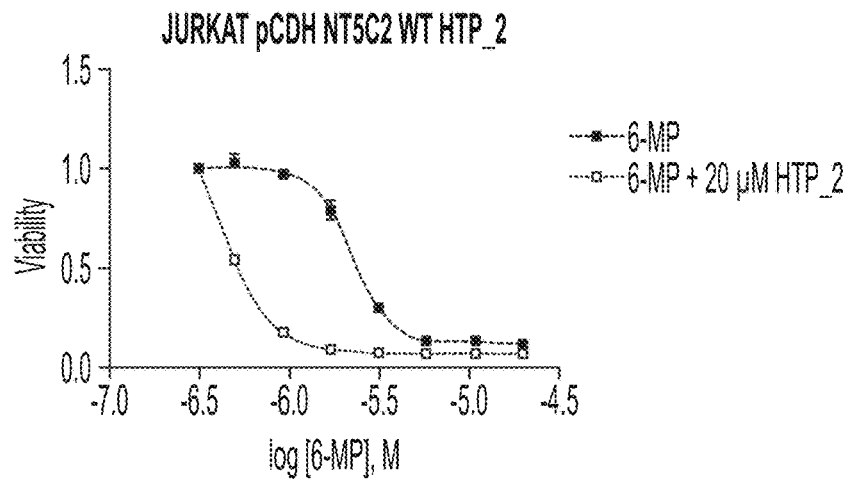
Figure 34K:
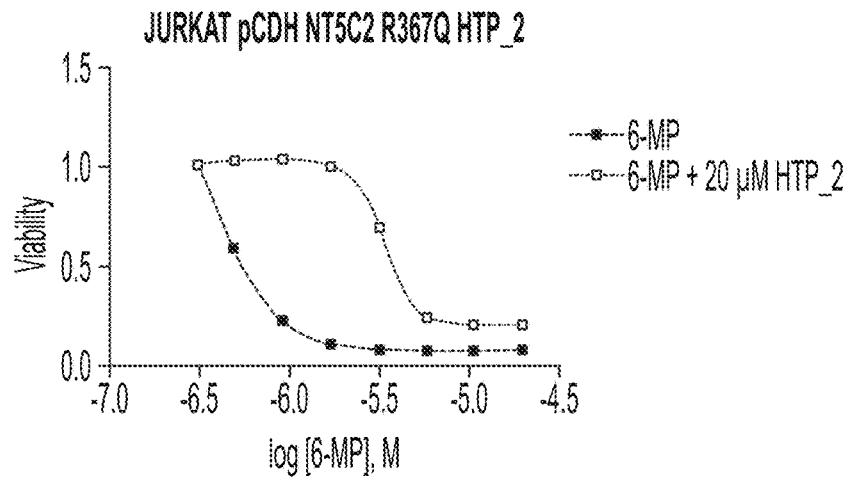

FIG. 33 is an example according to various embodiments, illustrating the NT5C2 inhibition response for varying amounts (μM) of a compound according to Formula 33 (HTP_49).

Formula 33 (HTP_49)

FIG. 34A through K are examples according to various embodiments, illustrating inhibition and reversal of 6-MP resistance in NT5C2 mutant acute lymphoblastic leukemia of compounds according to Formula 1 (HTP_2).

Figure 35A:
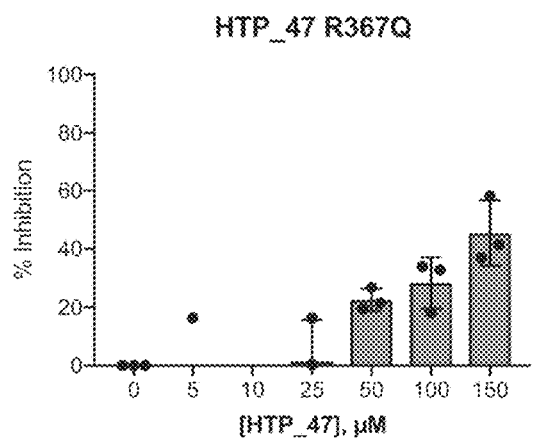
FIG. 35A through 35P are examples according to various embodiments, illustrating inhibition and reversal of 6-MP resistance in NT5C2 mutant acute lymphoblastic leukemia of compounds according to Formula 31 (HTP_47).
Figure 35B:
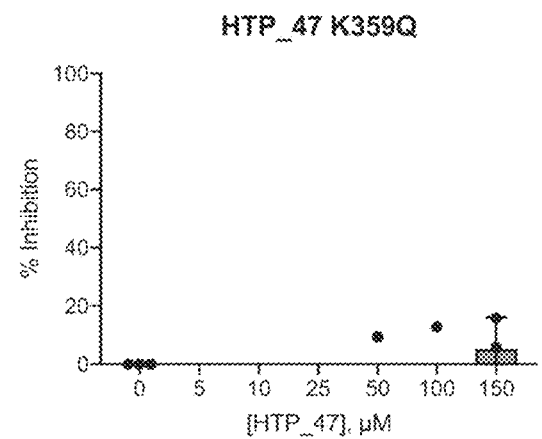
FIG. 35B is an example according to various embodiments, illustrating inhibitory activity of HTP_47 against recombinant NT5C2 K359Q protein in malachite green assays.
Figure 35C:
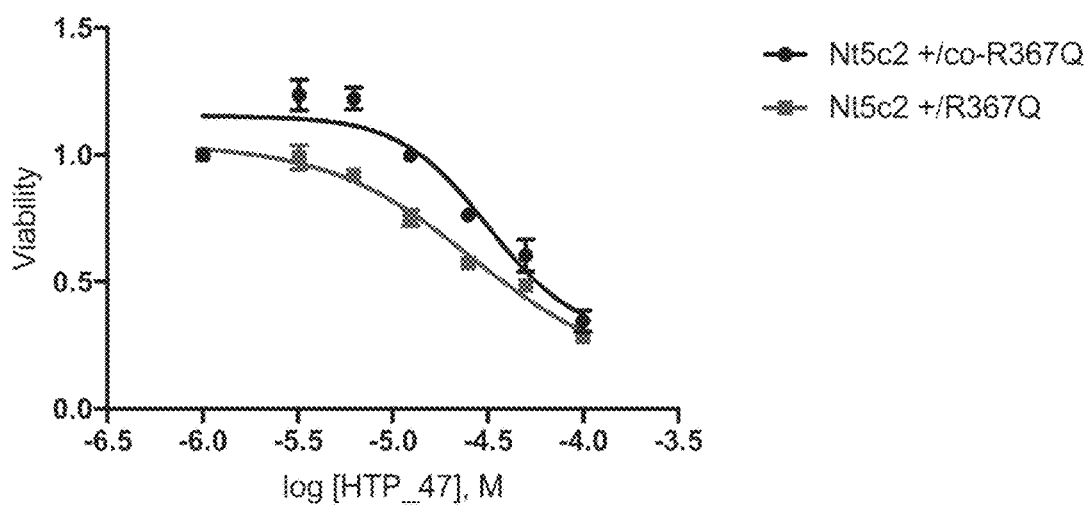
FIG. 35C is an example according to various embodiments, illustrating HTP_47 effects in cell viability in isogenic mouse T-ALL lymphoblasts with a wild type Nt5c2 (NT5C2+/co-R367Q) or a mutant Nt5c2 genotype (Nt5c2+/R367Q).
Figure 35D:
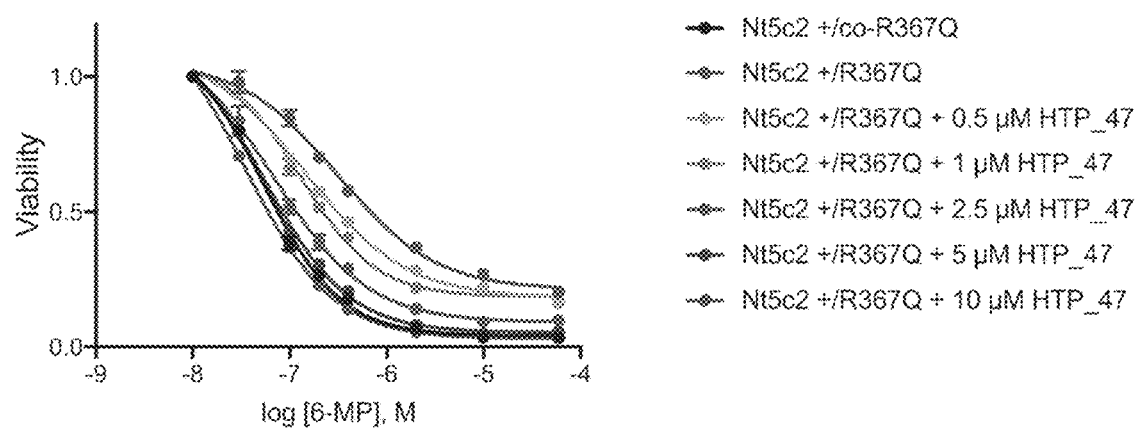
FIG. 35D is an example according to various embodiments, illustrating responses to 6-MP treatment in isogenic mouse T-ALL lymphoblasts with a wild type Nt5c2 (NT5C2+/co-R367Q) or a mutant Nt5c2 genotype (Nt5c2+/R367Q) measured as cell viability in presence of increasing concentrations of the HTP_47 NT5C2 inhibitor.
Figure 35E:
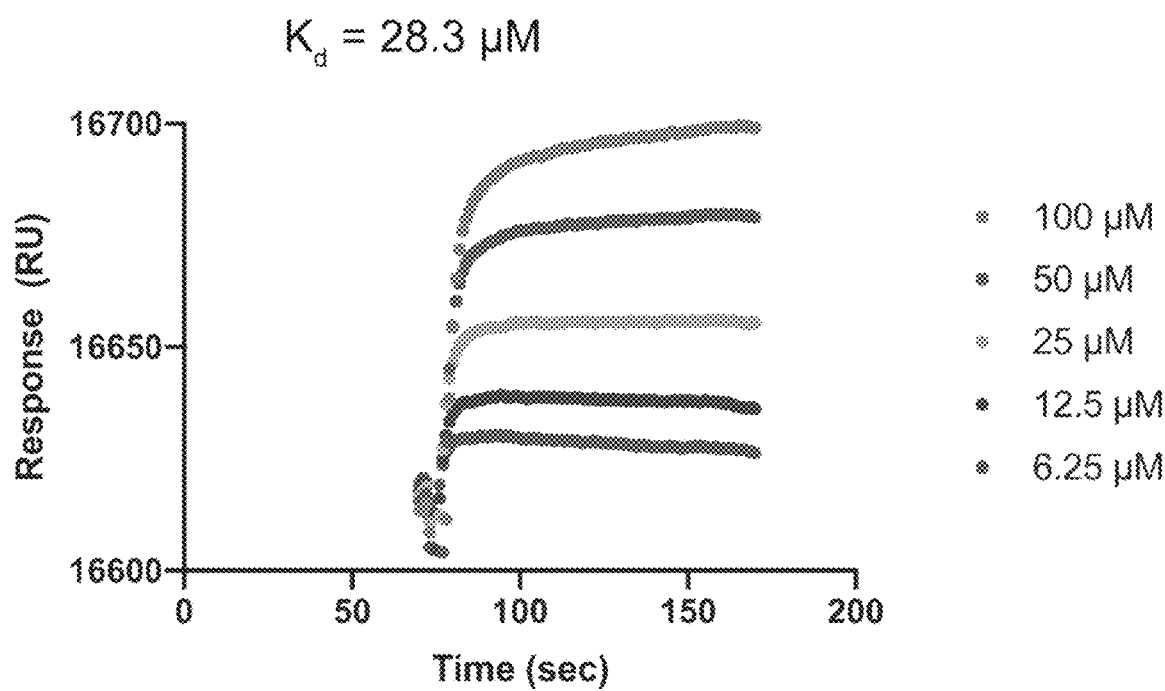
FIG. 35E is an example according to various embodiments, illustrating surface plasmon resonance analysis (Biacore) of HTP_47 interaction with recombinant NT5C2 protein.
Figure 35F:
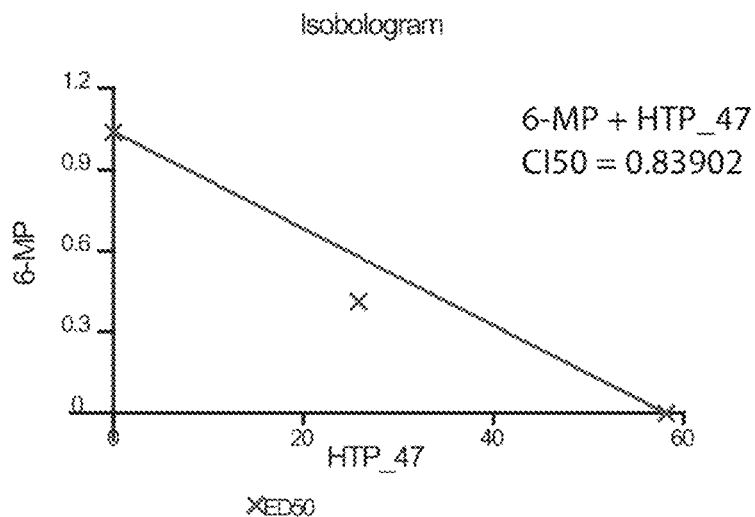
FIG. 35F Isobologram analysis of drug synergism between 6-MP and HTP_47 in mouse T-ALL lymphoblasts with a wild type Nt5c2 (NT5C2+/co-R367Q) genotype
Figure 35G:
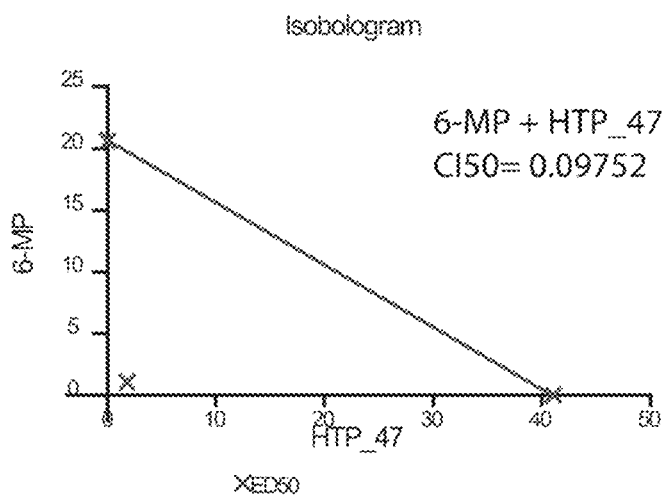
FIG. 35G is an example according to various embodiments, illustrating isobologram analysis of drug synergism between 6-MP and HTP_47 in mouse T-ALL lymphoblasts with a mutant Nt5c2 R367Q (NT5C2+/R367Q) genotype.
Figure 35H:
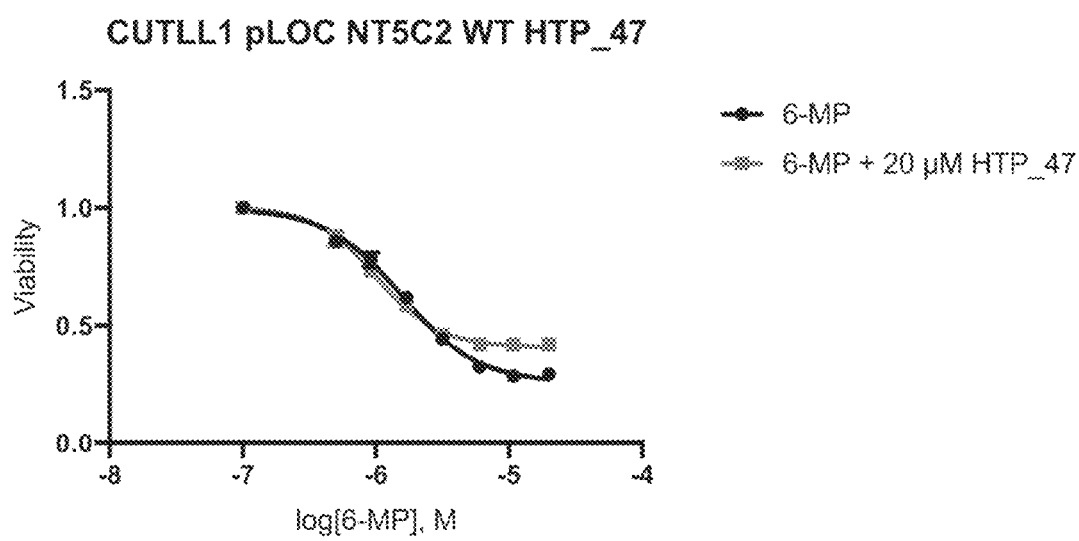
FIG. 35H is an example according to various embodiments, illustrating response to 6-MP measured as cell viability in human T-ALL cells (CUTLL1) expressing wild type NT5C2 in basal conditions and in presence of the HTP_47 NT5C2 inhibitor.
Figure 35I:
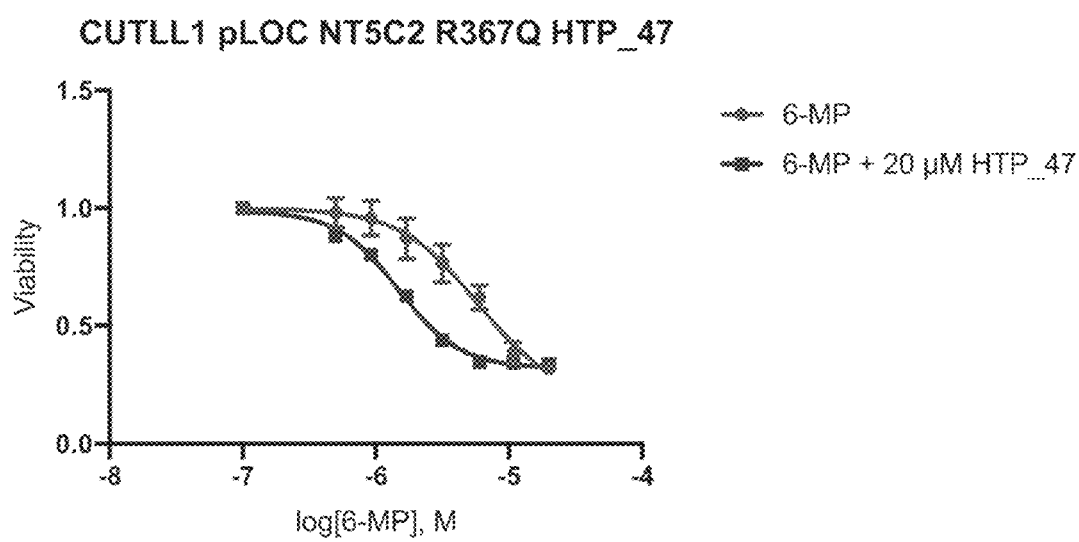
FIG. 35I is an example according to various embodiments, illustrating response to 6-MP measured as cell viability in human T-ALL cells (CUTLL1) expressing mutant NT5C2 R367Q in basal conditions and in presence of the HTP_2 NT5C2 inhibitor.
Figure 35J:
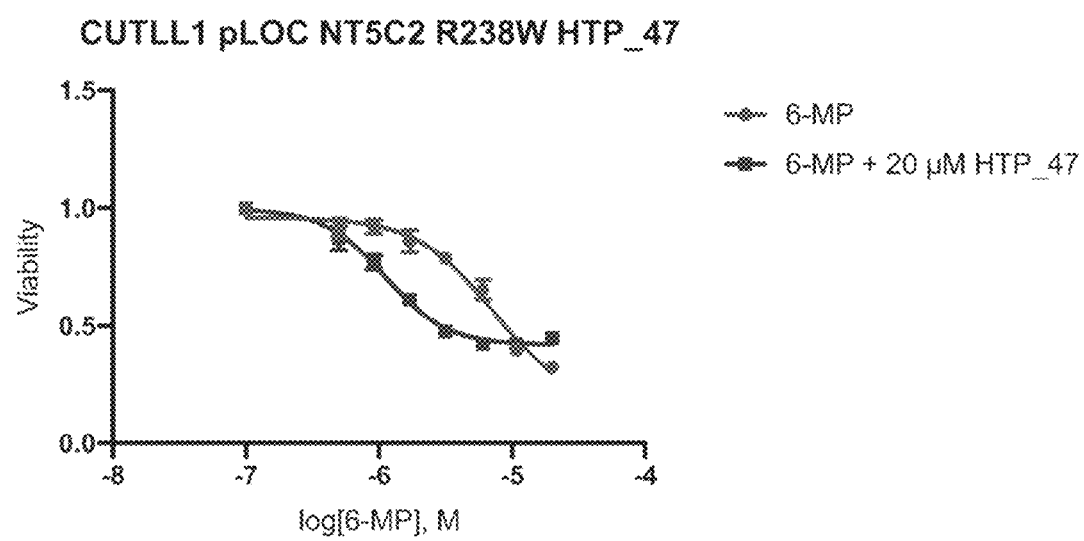
FIG. 35J is an example according to various embodiments, illustrating response to 6-MP measured as cell viability in human T-ALL cells (CUTLL1) expressing mutant NT5C2 R238W in basal conditions and in presence of the HTP_2 NT5C2 inhibitor.
Figure 35K:
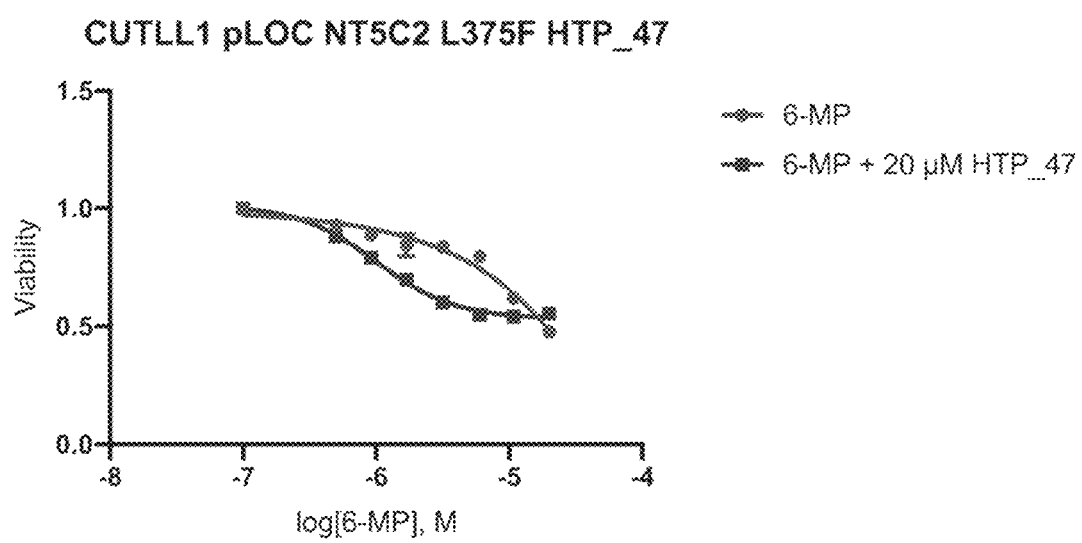
FIG. 35K is an example according to various embodiments, illustrating response to 6-MP measured as cell viability in human T-ALL cells (CUTLL1) expressing mutant NT5C2 L375F in basal conditions and in presence of the HTP_2 NT5C2 inhibitor.
Figure 35L:
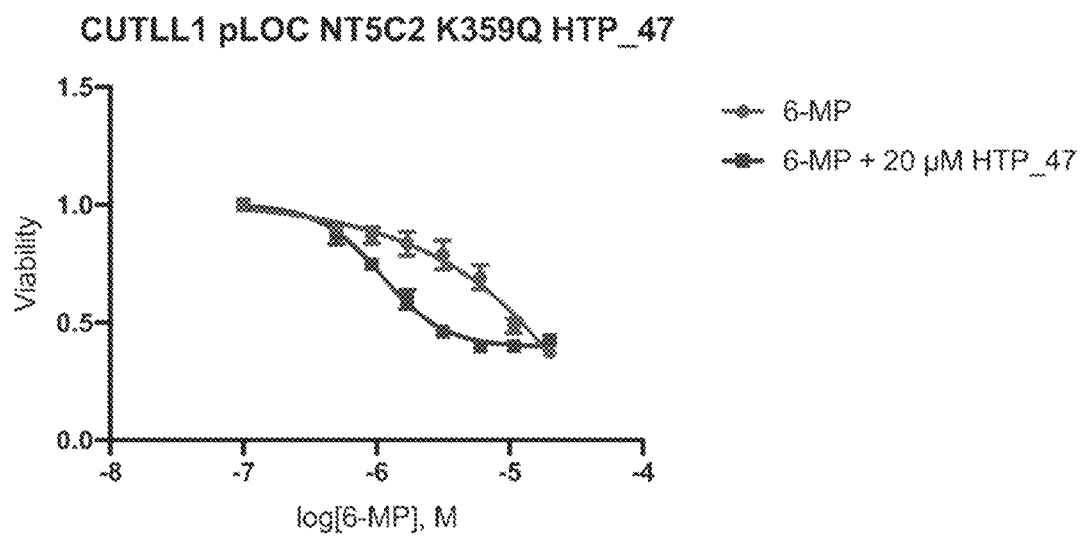
FIG. 35L is an example according to various embodiments, illustrating response to 6-MP measured as cell viability in human T-ALL cells (CUTLL1) expressing mutant NT5C2 K359Q in basal conditions and in presence of the HTP_2 NT5C2 inhibitor.
Figure 35M:
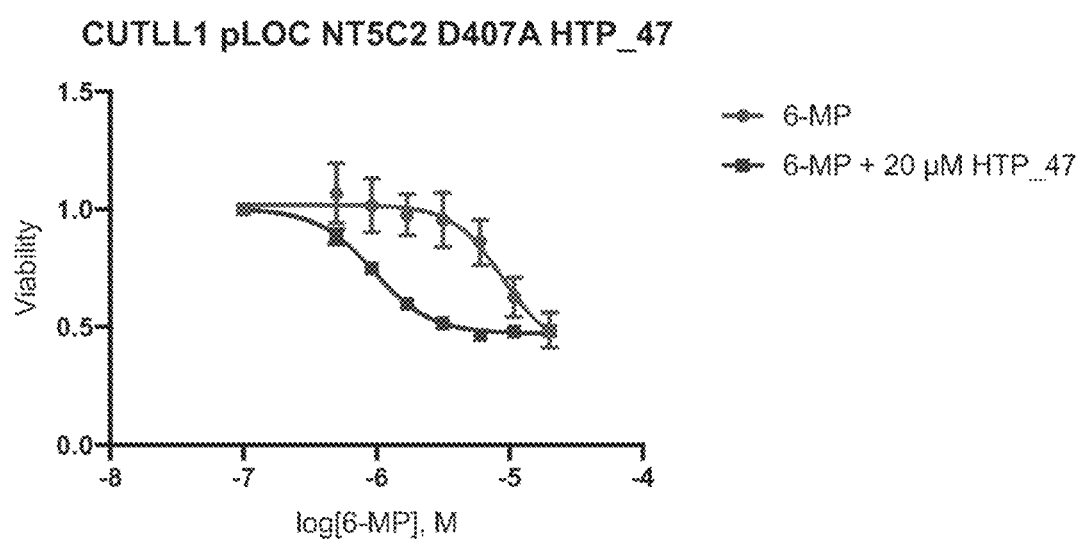
FIG. 35M is an example according to various embodiments, illustrating response to 6-MP measured as cell viability in human T-ALL cells (CUTLL1) expressing mutant NT5C2 D407A basal conditions and in presence of the HTP_2 NT5C2 inhibitor.
Figure 35N:
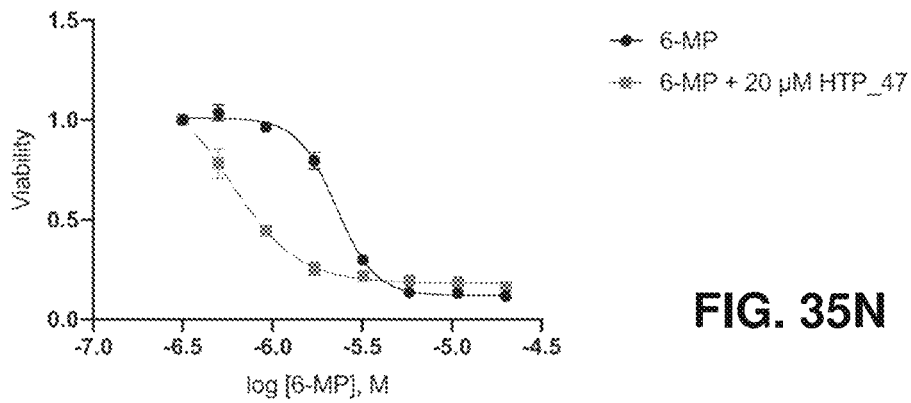
FIG. 35N is an example according to various embodiments, illustrating response to 6-MP measured as cell viability in human T-ALL cells (JURKAT) infected with an empty vector control in basal conditions and in presence of the HTP_47 NT5C2 inhibitor.
Figure 35O:
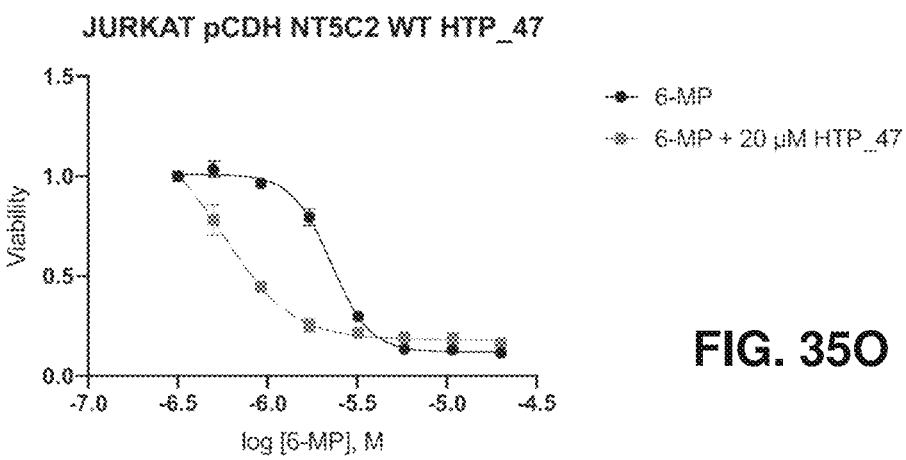
Figure 35P:
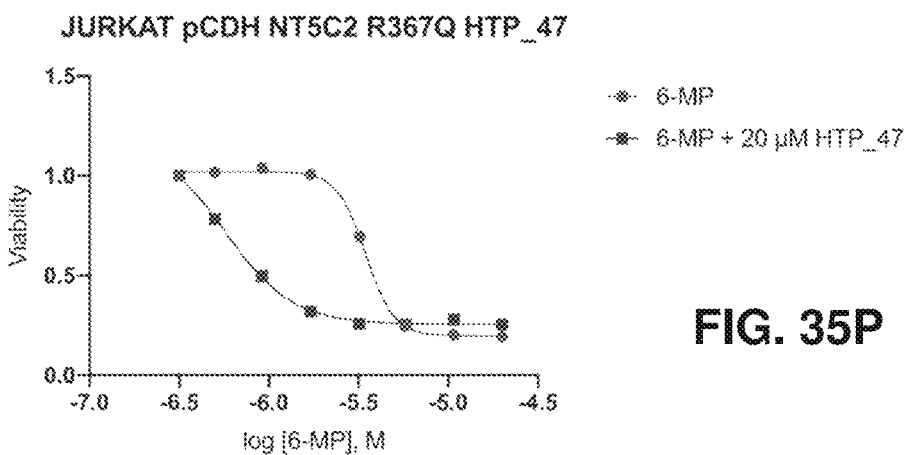

FIG. 35A through 35P are examples according to various embodiments, illustrating inhibition and reversal of 6-MP resistance in NT5C2 mutant acute lymphoblastic leukemia of compounds according to Formula 31 (HTP_47).

Figure 36:
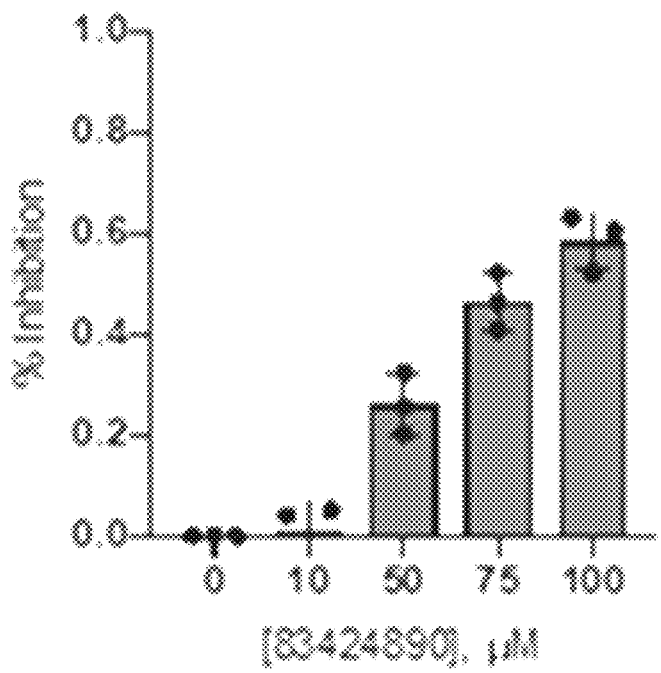
FIG. 36 is an example according to various embodiments, illustrating the NT5C2 inhibition response for varying amounts (μM) of a compound according to Formula 34.

FIG. 36 is an example according to various embodiments, illustrating the NT5C2 inhibition response for varying amounts (μM) of a compound according to Formula 34.

Formula 34

The structure according to Formula 35 show no NT5C2 inhibition activity.

Formula 35

The structure according to Formula 36 show no NT5C2 inhibition activity.

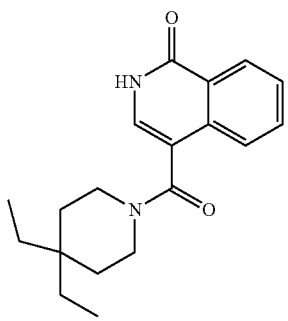

Formula 36

The structure according to Formula 37 show no NT5C2 inhibition activity.

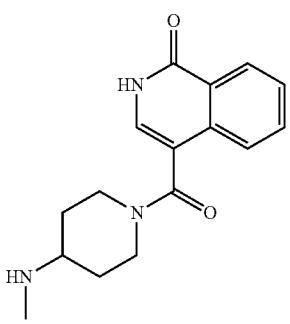

Formula 37

The structure according to Formula 38 did not dissolve and, therefore, no NT5C2 inhibition activity was observed.

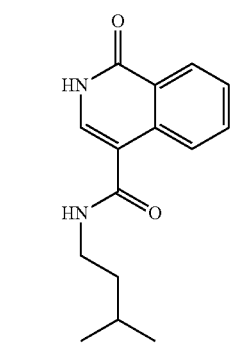

Formula 38

The structure according to Formula 39 show no NT5C2 inhibition activity.

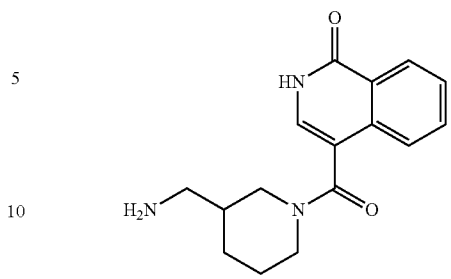

Formula 39

Figure 37:
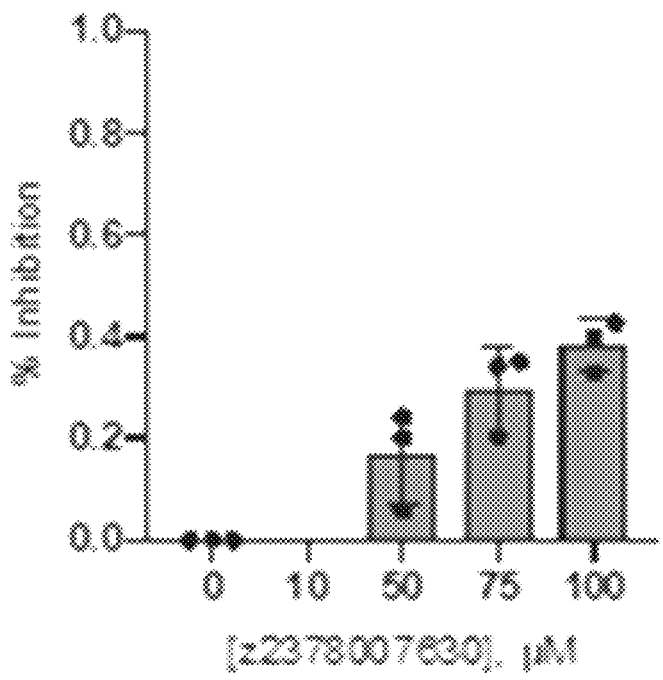
FIG. 37 is an example according to various embodiments, illustrating the NT5C2 inhibition response for varying amounts (μM) of a compound according to Formula 40.

FIG. 37 is an example according to various embodiments, illustrating the NT5C2 inhibition response for varying amounts (μM) of a compound according to Formula 40.

Formula 40

The structure according to Formula 41 show no NT5C2 inhibition activity.

Formula 41

Figure 38A:
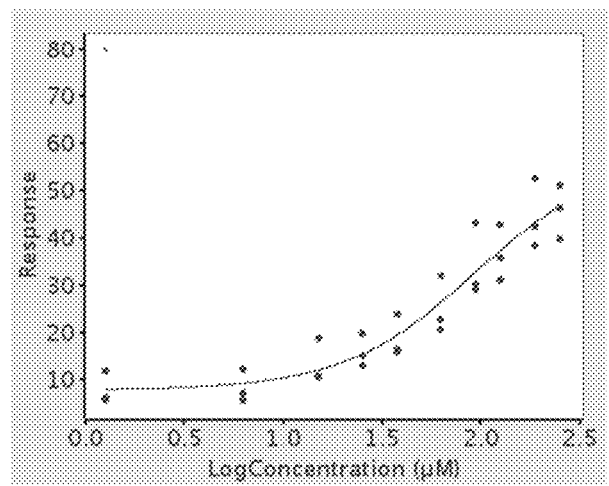
FIG. 38A through 38P are examples according to various embodiments, illustrating inhibition and reversal of 6-MP resistance in NT5C2 mutant acute lymphoblastic leukemia of a compound according to Formula 34.
Figure 38B:
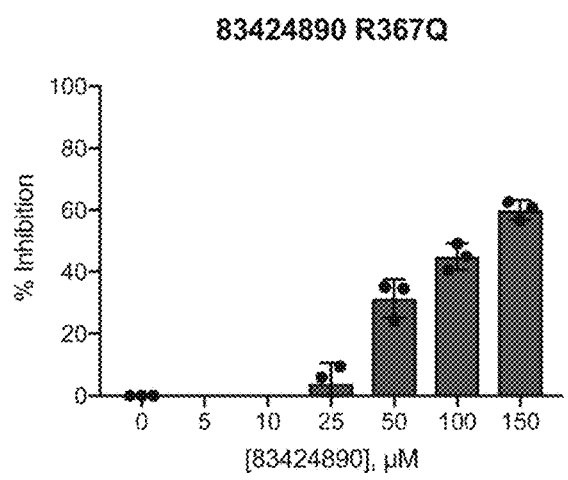
FIG. 38B is an example according to various embodiments, illustrating inhibitory activity of compound 83424890 presented in Formula 34 against recombinant NT5C2 R367Q protein in malachite green assays.
Figure 38C:
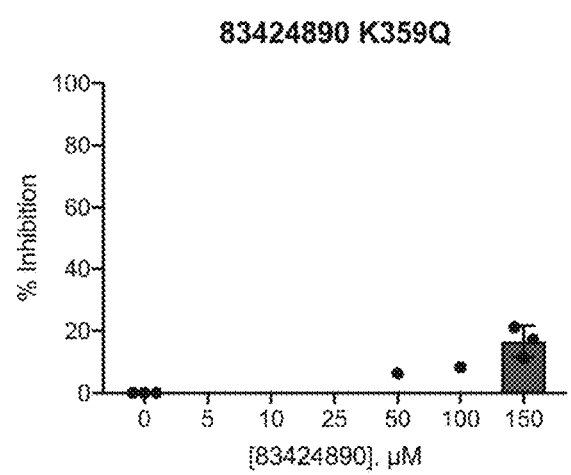
FIG. 38C is an example according to various embodiments, illustrating inhibitory activity of compound 83424890 presented in Formula 34 against recombinant NT5C2 K359Q protein in malachite green assays.
Figure 38D:
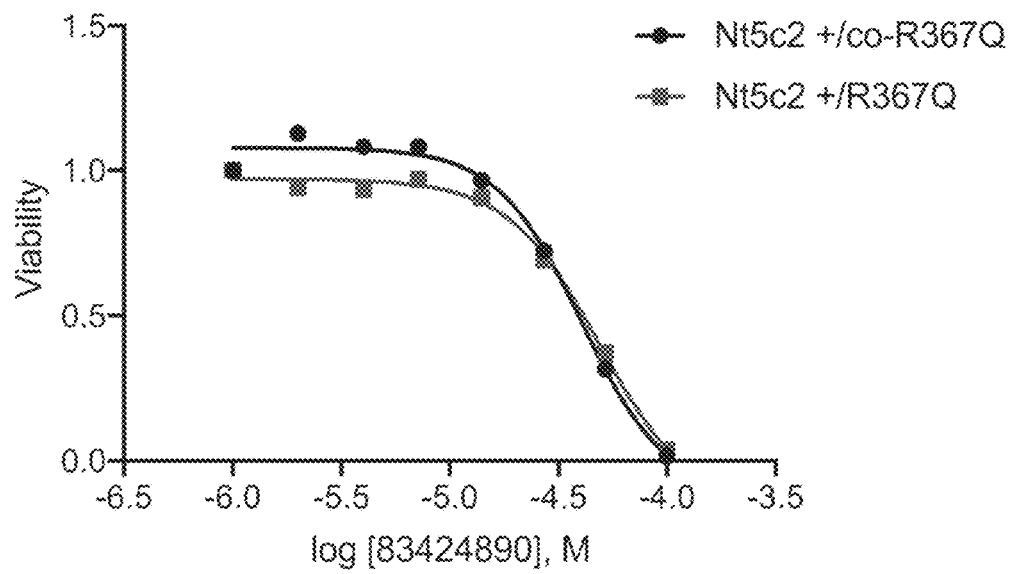
FIG. 38D is an example according to various embodiments, illustrating effects of compound 83424890 presented in Formula 34 in cell viability in isogenic mouse T-ALL lymphoblasts with a wild type Nt5c2 (NT5C2+/co-R367Q) or a mutant Nt5c2 genotype (Nt5c2+/R367Q).
Figure 38E:
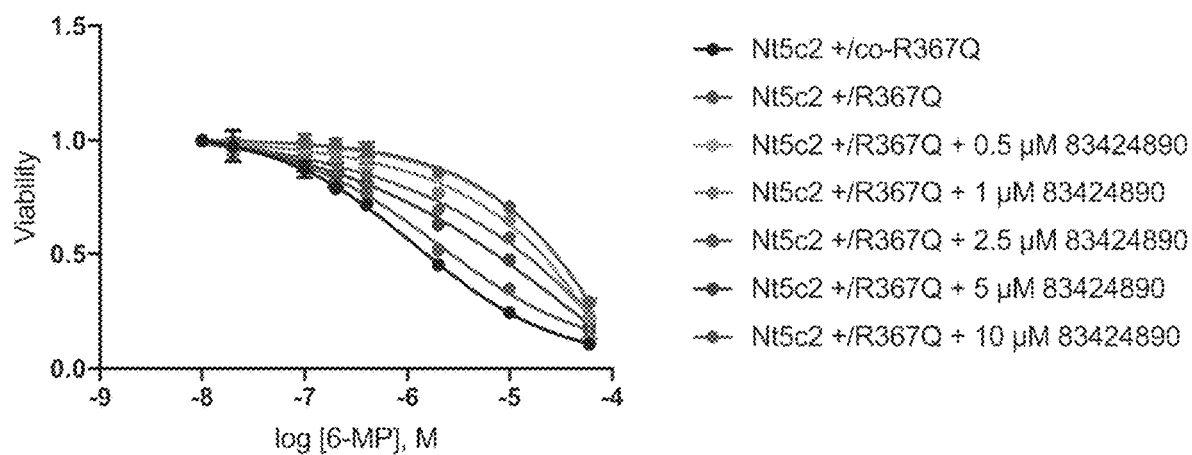
FIG. 38E is an example according to various embodiments, illustrating responses to 6-MP treatment in isogenic mouse T-ALL lymphoblasts with a wild type Nt5c2 (NT5C2+/co-R367Q) or a mutant Nt5c2 genotype (Nt5c2+/R367Q) measured as cell viability in presence of increasing concentrations of the NT5C2 inhibitor compound 83424890 presented in Formula 34.
Figure 38F:
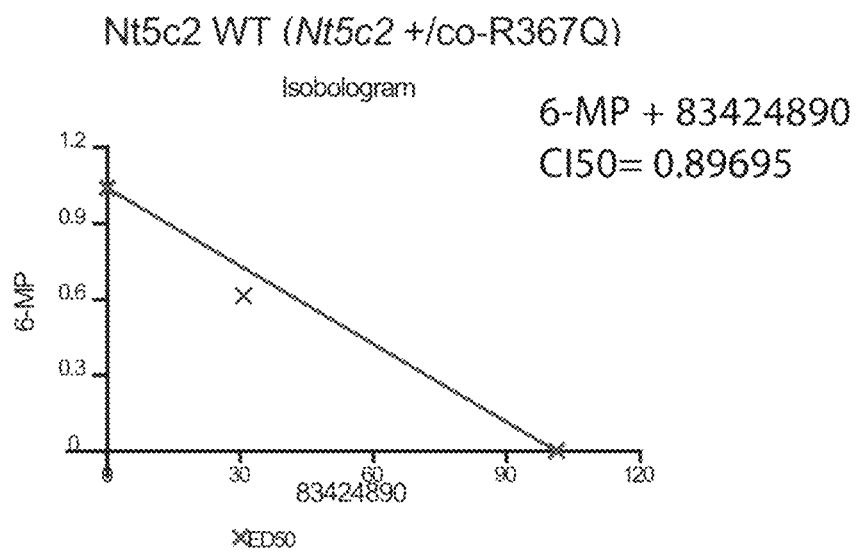
FIG. 38F is an example according to various embodiments, illustrating isobologram analysis of drug synergism between 6-MP and compound 83424890 presented in Formula 34 in mouse T-ALL lymphoblasts with a wild type Nt5c2 (NT5C2+/co-R367Q) genotype.
Figure 38G:
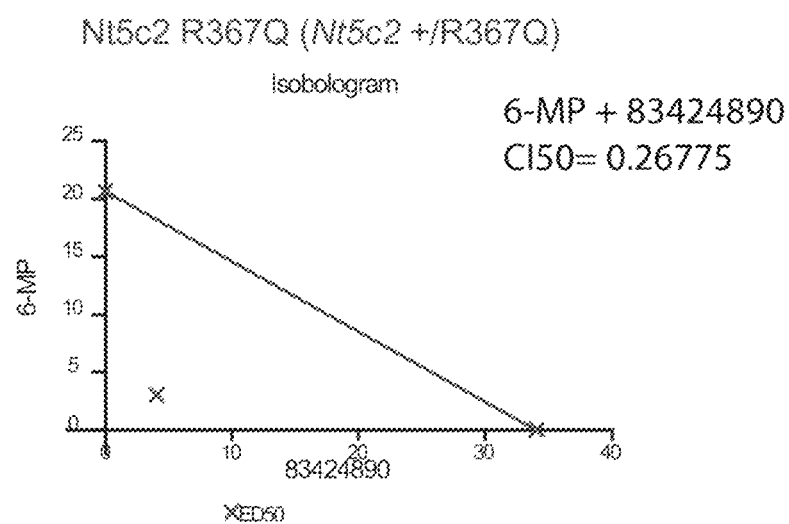
FIG. 38G is an example according to various embodiments, illustrating isobologram analysis of drug synergism between 6-MP and compound 83424890 presented in Formula 34 in mouse T-ALL lymphoblasts with a mutant Nt5c2 R367Q (NT5C2+/R367Q) genotype.
Figure 38H:
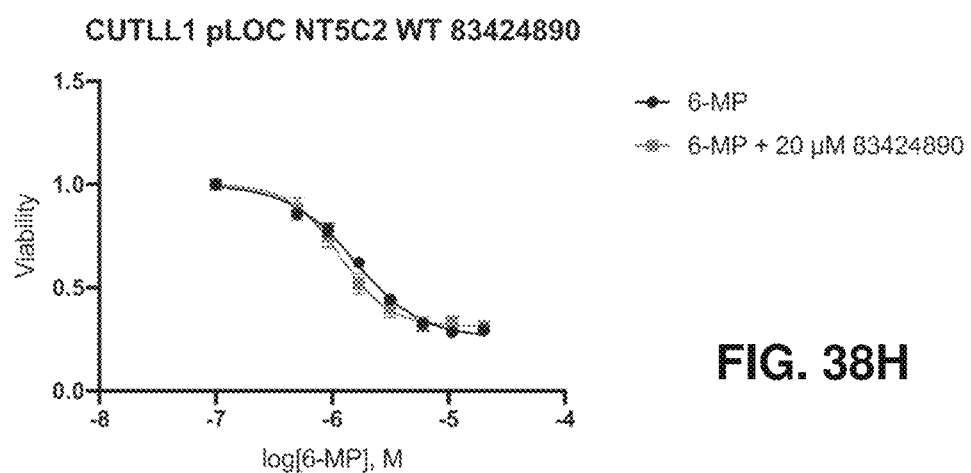
FIG. 38H is an example according to various embodiments, illustrating response to 6-MP measured as cell viability in human T-ALL cells (CUTLL1) expressing wild type NT5C2 in basal conditions and in presence of the NT5C2 inhibitor compound 83424890 presented in Formula 34.
Figure 38I:
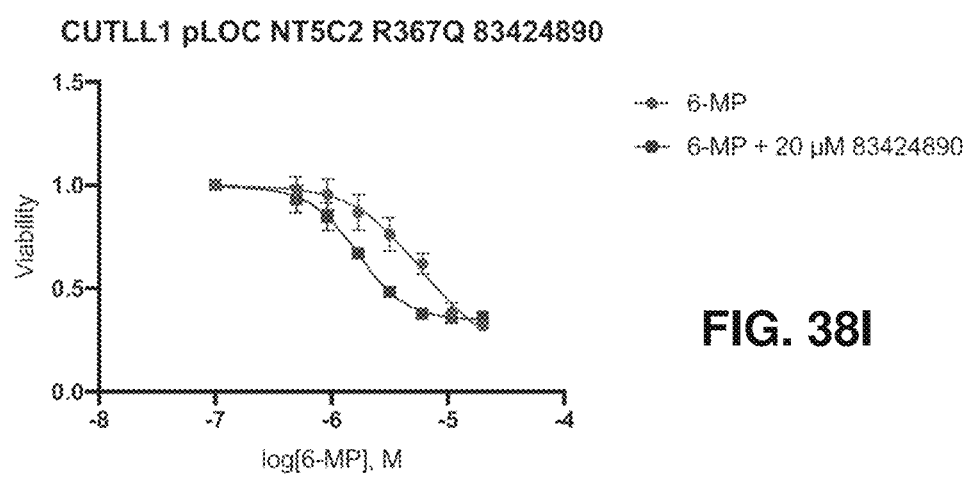
FIG. 38I is an example according to various embodiments, illustrating response to 6-MP measured as cell viability in human T-ALL cells (CUTLL1) expressing mutant NT5C2 R367Q in basal conditions and in presence of the NT5C2 inhibitor compound 83424890 presented in Formula 34.
Figure 38J:
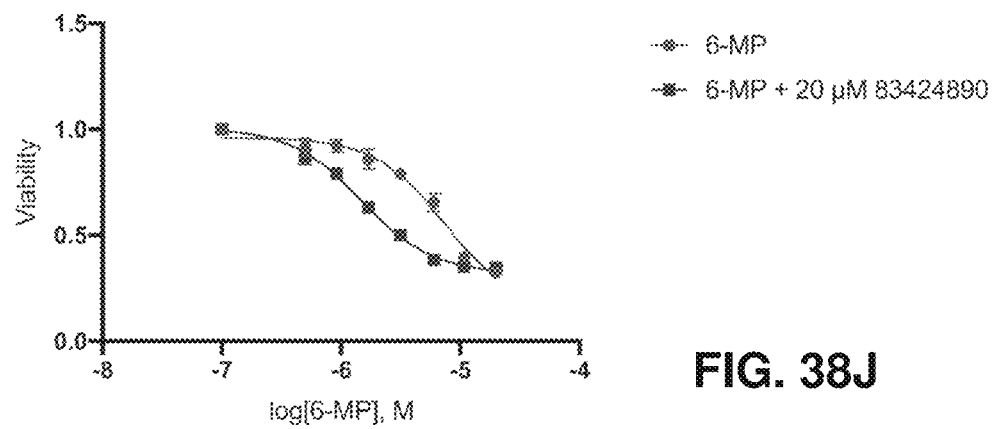
FIG. 38J is an example according to various embodiments, illustrating response to 6-MP measured as cell viability in human T-ALL cells (CUTLL1) expressing mutant NT5C2 R238W in basal conditions and in presence of the NT5C2 inhibitor compound 83424890 presented in Formula 34.
Figure 38K:
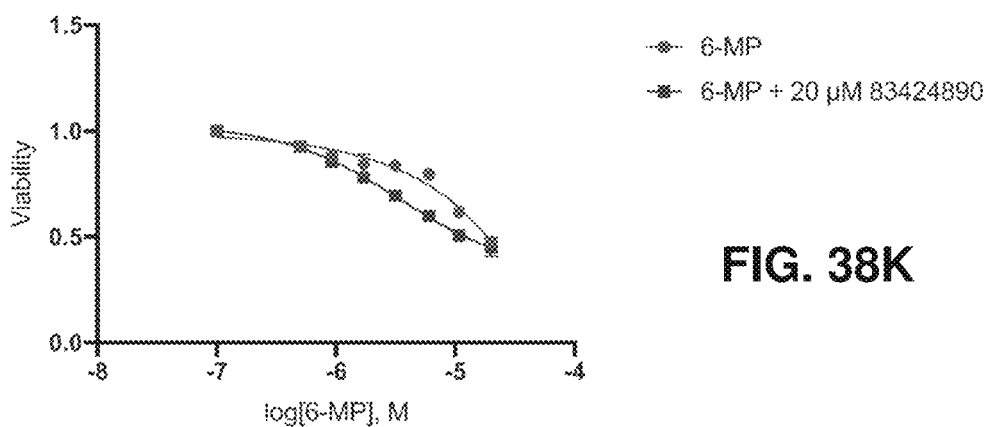
FIG. 38K is an example according to various embodiments, illustrating response to 6-MP measured as cell viability in human T-ALL cells (CUTLL1) expressing mutant NT5C2 L375F in basal conditions and in presence of the NT5C2 inhibitor compound 83424890 presented in Formula 34.
Figure 38L:
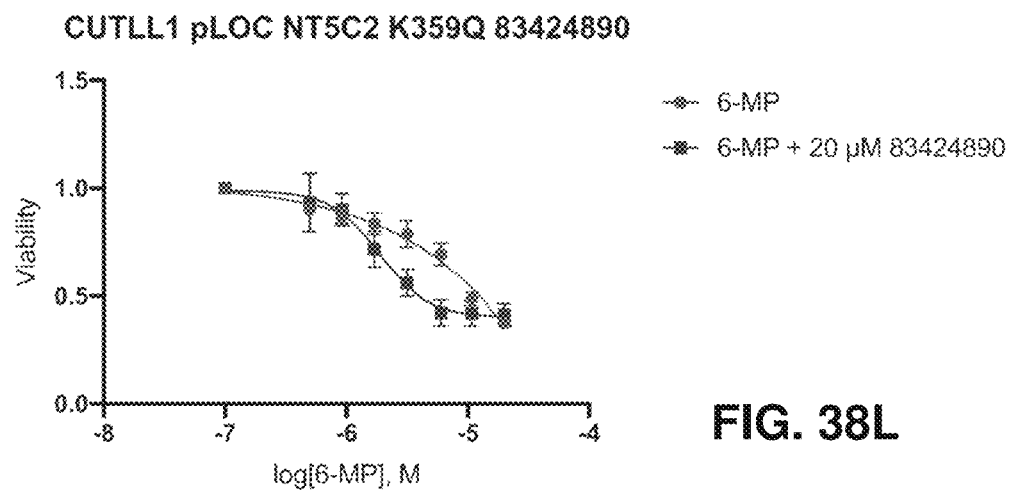
FIG. 38L is an example according to various embodiments, illustrating response to 6-MP measured as cell viability in human T-ALL cells (CUTLL1) expressing mutant NT5C2 K359Q in basal conditions and in presence of the NT5C2 inhibitor compound 83424890 presented in Formula 34.
Figure 38M:
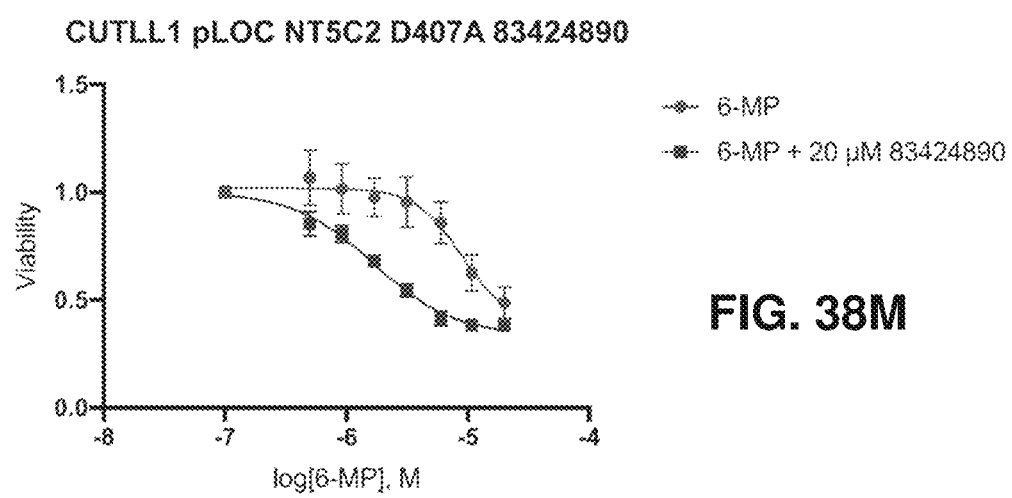
FIG. 38M is an example according to various embodiments, illustrating response to 6-MP measured as cell viability in human T-ALL cells (CUTLL1) expressing mutant NT5C2 D407A in basal conditions and in presence of the NT5C2 inhibitor compound 83424890 presented in Formula 34.
Figure 38N:
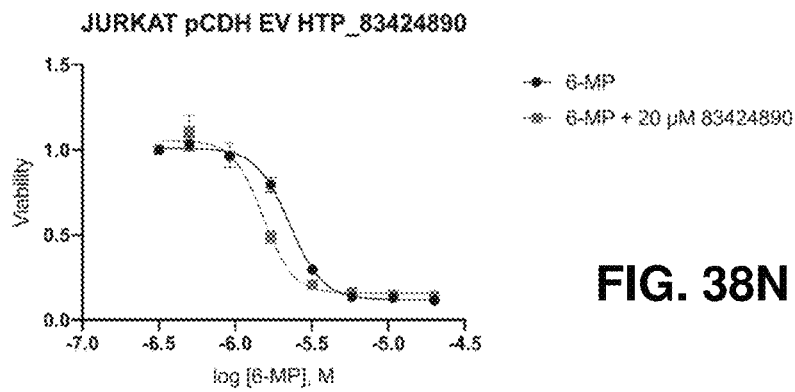
FIG. 38N is an example according to various embodiments, illustrating response to 6-MP measured as cell viability in human T-ALL cells (JURKAT) infected with an empty vector control in basal conditions and in presence of the NT5C2 inhibitor compound 83424890 presented in Formula 34.
Figure 38O:
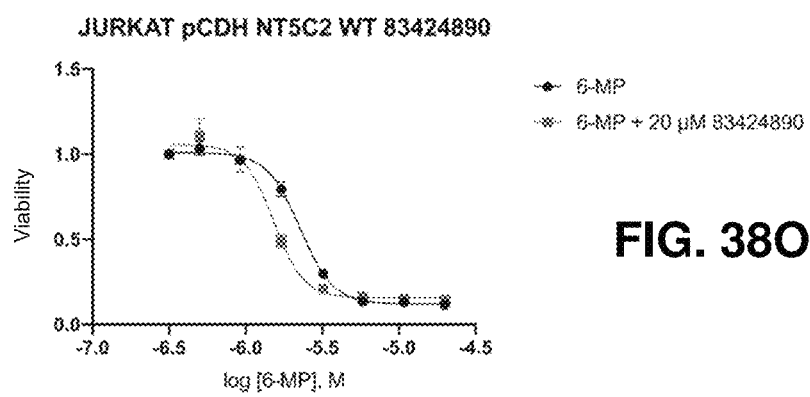
FIG. 38O is an example according to various embodiments, illustrating response to 6-MP measured as cell viability in human T-ALL cells (JURKAT) infected with a vector expressing wild type NT5C2 in basal conditions and in presence of the NT5C2 inhibitor compound 83424890 presented in Formula 34.
Figure 38P:
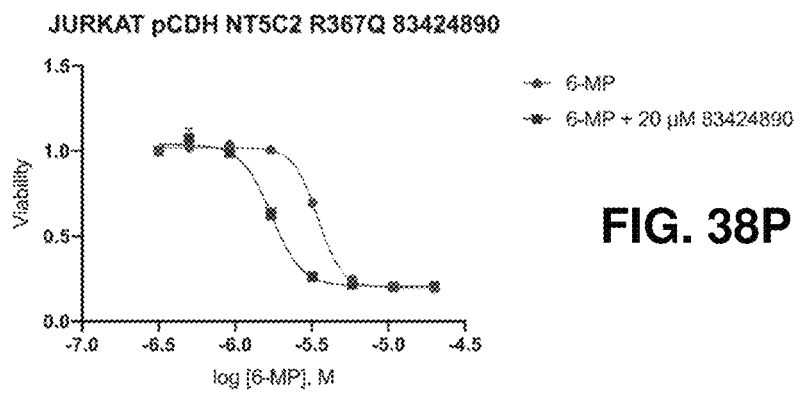

FIG. 38A through P are examples according to various embodiments, illustrating inhibition and reversal of 6-MP resistance in NT5C2 mutant acute lymphoblastic leukemia of a compound according to Formula 34.

Compositions and Formulations

The NT5C2 inhibitors and related compounds discussed herein are contemplated for use as pharmaceutical compositions, which are useful for treatment of acute lymphoblastic leukemia. Therefore, the enumerated compounds are formulated into pharmaceutical compositions, including a carrier, for administration to human subjects in a biologically compatible form suitable for administration in vivo. The present invention thus provides a pharmaceutical composition comprising one or more enumerated compounds in admixture with a pharmaceutically acceptable diluent and/or carrier. The pharmaceutically-acceptable carrier must be "acceptable" in the sense of being compatible with the other ingredients of the composition and not deleterious to the recipient thereof.

Pharmaceutically acceptable carriers are well known in the art (see, e.g., Remington, The Science and Practice of Pharmacy (21 stEdition, Lippincott Williams and Wilkins, Philadelphia, PA) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Carriers suitable for a selected dosage form and intended route of administration are well known in the art, and acceptable carriers for a chosen dosage form and method of administration can be determined using ordinary skill in the art.

The pharmaceutical formulations of the present invention are prepared by methods well-known in the pharmaceutical arts. For example, the enumerated compounds are brought into association with a carrier and/or diluent, as a suspension or solution. Optionally, one or more accessory ingredients (e.g., buffers, flavoring agents, surface active agents, and the like) also are added. The choice of carrier is well within the prevue of the person of ordinary skill in the relevant art and is determined by the solubility and chemical nature of the compounds, chosen route of administration and standard pharmaceutical practice. These accessory ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, sucrose and acacia; (3) humectants, such as glycerol; (4) disintegrating agents, such as agar-agar, calcium carbonate, potato or tapioca starch, alginic acid, certain silicates, sodium starch glycolate, cross-linked sodium carboxymethyl cellulose and sodium carbonate; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as talc, calcium stearate, magnesium stearate, solid polyethylene glycols, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as water or other solvents; (14) preservatives; (15) surface-active agents; (16) dispersing agents; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

For administration to a suitable subject, preferably to a human patient suffering from or suspected of suffering from acute lymphoblastic leukemia, the compounds described here are prepared according to methods known in the art into suitable formulations for any route of administration and suitable doses. Suitable subjects for administration and treatment can be any mammal, including rats, mice, dogs, cats, farm animals such as cattle, sheep, horses and the like or any mammal.

Dosing and Dosage Forms

The appropriate dose of an enumerated compound depends upon a number of factors within the ken of the ordinarily skilled physician, veterinarian, or researcher for example, the identity, size, and condition of the subject or sample being treated, further depending upon the route by which the composition is to be administered, the frequency of administration, the severity of the disease, and the effect which the practitioner desires the an active agent to have. Furthermore, appropriate doses of an active agent depend upon the potency with respect to the expression or activity to be modulated. Such appropriate doses may be determined using the assays described herein or which are convenient to the practitioner and know in the art. When one or more of these active agents are to be administered to an animal (e.g., a human), a relatively low dose may be prescribed at first, with the dose subsequently increased until an appropriate response is obtained. In addition, the specific dose level for any particular subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Dosages and regimens for administration are determined by the person of skill, including physicians. Administration of compositions, including the compounds described here, can be performed a single time, or repeated at intervals, such as by continuous infusion or repeated oral doses, over a period of time, four times daily, twice daily, daily, every other day, weekly, monthly, or any interval to be determined by the skilled artisan based on the subject involved. Treatment can involve administration over a period of one day only, a week, a month, several months, years, or over a lifetime. Regimens and duration can vary according to any system known in the art, as is known to the skilled person.

Pharmaceutical compositions suitable for oral administration may be in the form of capsules, cachets, pills, tablets, powders, granules, a solution or a suspension in an aqueous or non-aqueous liquid, an oil-in-water or water-in-oil liquid emulsion, an elixir or syrup, a pastille, a bolus, an electuary or a paste. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

Liquid dosage forms for oral administration include pharmaceutically-acceptable emulsions, microemulsions, solutions, suspensions, syrups and elixirs. The liquid dosage forms may contain suitable inert diluents commonly used in the art. Besides inert diluents, the oral compositions may also include adjuvants, such as wetting agents, emulsifying and suspending agents, sweetening, flavoring, coloring, perfuming and preservative agents. Suspensions may contain suspending agents.

Pharmaceutical compositions for rectal or vaginal administration may be presented as a suppository, which maybe prepared by mixing one or more active ingredient(s) with one or more suitable nonirritating carriers which are solid at room temperature, but liquid at body temperature and, therefore, will melt in the rectum or vaginal cavity and release the active compound. Pharmaceutical compositions which are suitable for vaginal administration also include pessaries, tampons, creams, gels, pastes, foams or spray formulations containing such pharmaceutically-acceptable carriers as are known in the art to be appropriate.

Dosage forms for the topical or transdermal administration include powders, sprays, ointments, pastes, creams, lotions, gels, solutions, patches, drops and inhalants. The active agent(s)/compound(s) may be mixed under sterile conditions with a suitable pharmaceutically-acceptable carrier. The ointments, pastes, creams and gels may contain excipients. Powders and sprays may contain excipients and propellants.

Pharmaceutical compositions suitable for parenteral administrations comprise one or more agent(s)/compound(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain suitable antioxidants, buffers, solutes which render the formulation isotonic with the blood of the intended recipient, or suspending or thickening agents. Proper fluidity can be maintained, for example, by the use of coating materials, by the maintenance of the required particle size in the case of dispersions, and by the use of surfactants. These compositions may also contain suitable adjuvants, such as wetting agents, emulsifying agents and dispersing agents. It may also be desirable to include isotonic agents. In addition, prolonged absorption of the injectable pharmaceutical form may be brought about by the inclusion of agents which delay absorption.

In some cases, in order to prolong the effect of a drug (e.g., pharmaceutical formulation), it is desirable to slow its absorption from subcutaneous or intramuscular injection. This may be accomplished by the use of a liquid suspension of crystalline or amorphous material having poor water solubility.

The rate of absorption of the active agent/drug then depends upon its rate of dissolution which, in turn, may depend upon crystal size and crystalline form. Alternatively, delayed absorption of a parenterally-administered agent/drug may be accomplished by dissolving or suspending the active agent/drug in an oil vehicle. Injectable depot forms may be made by forming microencapsule matrices of the active ingredient in biodegradable polymers. Depending on the ratio of the active ingredient to polymer, and the nature of the particular polymer employed, the rate of active ingredient release can be controlled. Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

Salts

Salts of the enumerated compounds disclosed herein include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like. Salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

Stereoisomers

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers, optical isomers, and diastereomers.

The terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that compounds of the present invention having a chiral center may exist in and be isolated in optically active and racemic forms. Some compounds may exhibit polymorphism. It is to be understood that the present invention encompasses any racemic, optically-active, diastereomeric, polymorphic, or stereoisomeric form, or mixtures thereof, of enumerated compound, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

As noted, the enumerated compounds may contain one or more chiral centers and/or double bonds and therefore, may exist as stereoisomers, such as double-bond isomers (i.e., geometric isomers such as E and Z), enantiomers or diastereomers. Thus, reference to enumerated compound includes each of the isolated stereoisomeric forms (such as the enantiomerically pure isomers, the E and Z isomers, and etc.) as well as mixtures of stereoisomers in varying degrees of chiral purity or percentage of E and Z, including racemic mixtures, mixtures of diastereomers, and mixtures of E and Z isomers of the compound. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted olefin isomer. When the chemical name does not specify the isomeric form of the compound, it denotes any one of the possible isomeric forms or a mixture of those isomeric forms of the compound.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

The compounds described herein may also exist in several tautomeric forms. The term "tautomer" as used herein refers to isomers that change into one another with great ease by a proton or an alkyl shift from one atom of a molecule to another atom of the same molecule so that they can exist together in equilibrium. For example, ketone and enol are two tautomeric forms of one compound.

What is claimed is:

1. A method of treating cancer comprising administering a therapeutically effective amount of a compound, having the structure:

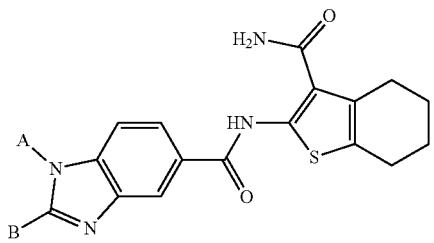

wherein A is selected from the group consisting of hydrogen and methyl, and wherein B is selected from the group consisting of hydrogen and methyl.

2. The method of claim 1, wherein the compound inhibits NT5C2 nucleotidase.

3. The method of claim 1, wherein the compound synergistically decreases cell viability of NT5C2 R367Q mutant lymphoblasts when used in combination with 6-mercaptopurine (6-MP) to treat a cancer.

4. The method of claim 3, wherein the cancer is acute lymphoblastic leukemia.

5. The method of claim 1, further comprising co-administering an adjunct cancer therapeutic agent.

6. The method of claim 5, wherein the adjunct cancer therapeutic agent is a purine analog.

7. The method of claim 1, wherein the cancer is acute lymphoblastic leukemia.

8. The method of claim 1, wherein the compound is in admixture with a pharmaceutically acceptable carrier.

9. A method of treating cancer comprising administering a therapeutically effective amount of a compound having the structure:

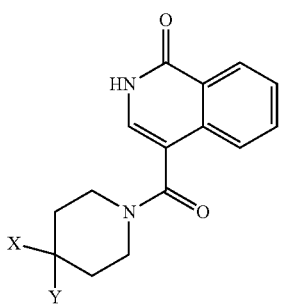

wherein X is selected from the group consisting of hydrogen and

N≡C∿, and
wherein Y is selected from the group consisting of

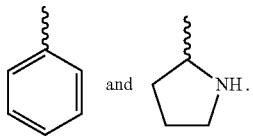

10. A method of claim 9, wherein the compound inhibits NT5C2 nucleotidase.

11. The method of claim 9, further comprising co-administering an adjunct cancer therapeutic agent.

12. The method of claim 11, wherein the adjunct cancer therapeutic agent comprises a purine analog.

13. The method of claim 9, wherein the cancer is acute lymphoblastic leukemia.

14. The method of claim 9, wherein the compound is in admixture with a pharmaceutically acceptable carrier.

15. The method of claim 14 further comprising administration of an adjunct cancer therapeutic agent.

16. The method of claim 15, wherein the adjunct cancer therapeutic agent is a purine analog.

17. The method of claim 9, wherein the cancer is acute lymphoblastic leukemia.

* * * * *